(12) United States Patent
Xu et al.

(10) Patent No.: US 10,711,287 B2
(45) Date of Patent: Jul. 14, 2020

(54) D-LACTATE DEHYDROGENASE, ENGINEERED STRAIN CONTAINING D-LACTATE DEHYDROGENASE AND CONSTRUCTION METHOD AND USE OF ENGINEERED STRAIN

(71) Applicant: Shanghai Jiao Tong University, Shanghai (CN)

(72) Inventors: Ping Xu, Shanghai (CN); Chao Li, Shanghai (CN); Fei Tao, Shanghai (CN); Hongzhi Tang, Shanghai (CN)

(73) Assignee: Shanghai Jiao Tong University, Shanghai (CN)

( * ) Notice: Subject to any disclaimer, the term of this patent is extended or adjusted under 35 U.S.C. 154(b) by 0 days.

(21) Appl. No.: 16/073,051

(22) PCT Filed: Jan. 25, 2017

(86) PCT No.: PCT/CN2017/072647
§ 371 (c)(1),
(2) Date: Jul. 26, 2018

(87) PCT Pub. No.: WO2017/129136
PCT Pub. Date: Aug. 3, 2017

(65) Prior Publication Data
US 2019/0040425 A1   Feb. 7, 2019

(30) Foreign Application Priority Data
Jan. 27, 2016 (CN) .......................... 2016 1 0056883

(51) Int. Cl.
| C12P 7/56 | (2006.01) |
| C12N 15/75 | (2006.01) |
| C12N 9/10 | (2006.01) |
| C12N 9/04 | (2006.01) |
| C12N 9/88 | (2006.01) |

(52) U.S. Cl.
CPC .............. *C12P 7/56* (2013.01); *C12N 9/0006* (2013.01); *C12N 9/1022* (2013.01); *C12N 15/75* (2013.01); *C12Y 101/01028* (2013.01)

(58) Field of Classification Search
None
See application file for complete search history.

(56) References Cited

U.S. PATENT DOCUMENTS

2012/0129231 A1   5/2012 Wang et al.
2019/0040425 A1   2/2019 Xu et al.

FOREIGN PATENT DOCUMENTS

| CN | 103547671 A | 1/2014 |
| CN | 105062938 A | 11/2015 |
| CN | 105907732 A | 8/2016 |

OTHER PUBLICATIONS

Genbank accession No. WP_013906894.1 GenBank Database (May 18, 2013).
Chao et al., "Carbon Flux Trapping: Highly Efficient Production of Polymer-Grade d-Lactic Acid with a Thermophilic d-Lactate Dehydrogenase", CHEMBIOCHEM, 2016, pp. 1491-1494, vol. 17:16.
Wang, "Evolution of D-lactate dehydrogenase activity from glycerol dehydrogenase and its utility for D-lactate production from lignocellulose", PNAS, Nov. 22, 2011, pp. 18920-18925, vol. 108:47.

*Primary Examiner* — Suzanne M Noakes
*Assistant Examiner* — Jae W Lee
(74) *Attorney, Agent, or Firm* — The Webb Law Firm

(57) ABSTRACT

Provided herein is D-lactate dehydrogenase, an engineered strain containing the D-lactate dehydrogenase, and a construction method and use of the engineered strain. The D-lactate dehydrogenase has unique properties and is from *Thermodesulfatator indicus*, and the D-lactate dehydrogenase has good thermophily and heat stability. By using the D-lactate dehydrogenase and the gene engineering reconstruction method, a fermentation product of the reconstructed *Bacillus licheniformis* can be redirected to optically-pure D-lactic acid with a high yield from naturally produced 2,3-butanediol, and the optical purity of the produced D-lactic acid reaches 99.9%; and raw materials for fermentation are low-cost, and a fermentation state is between an anaerobic fermentation state and a microaerobic fermentation state. By using the method for producing D-lactic acid through fermentation at high temperature, the production cost can be reduced, the production efficiency can be improved and there is a wide industrial application prospect for the method.

4 Claims, 7 Drawing Sheets

Specification includes a Sequence Listing.

SEQUENCE LISTING

```
<160> NUMBER OF SEQ ID NOS: 93

<210> SEQ ID NO 1
<211> LENGTH: 325
<212> TYPE: PRT
<213> ORGANISM: Thermodesulfatator indicus DSM 15286

<400> SEQUENCE: 1

Met Lys Val Ile Phe Phe Ser Met His Pro Tyr Glu Glu Glu Phe Leu
1               5                   10                  15

Gly Pro Ile Leu Pro Ser Asp Trp Asp Val Glu Met Thr Pro Asp Phe
            20                  25                  30

Leu Asp Glu Thr Thr Val Glu Lys Ala Lys Gly Ala Gln Val Val Ser
        35                  40                  45

Leu Phe Val Ser Asp Lys Ala Asp Gly Pro Val Leu Glu Ala Leu His
    50                  55                  60

Ser Tyr Gly Val Gly Leu Leu Ala Leu Arg Ser Ala Gly Tyr Asp His
65                  70                  75                  80

Ile Asp Ile Glu Thr Ala Lys Arg Leu Gly Ile Lys Val Val Asn Val
                85                  90                  95

Pro Ala Tyr Ser Pro His Ala Ile Ala Asp His Thr Leu Ala Ile Met
            100                 105                 110

Leu Ala Leu Ile Arg Arg Leu His Arg Ala His Asp Lys Val Arg Leu
        115                 120                 125

Gly Asp Phe Asp Leu Asp Gly Leu Met Gly Phe Asp Leu Asn Gly Lys
    130                 135                 140

Val Ala Gly Val Ile Gly Leu Gly Lys Ile Gly Arg Leu Val Ala Thr
145                 150                 155                 160

Arg Leu Lys Ala Phe Gly Cys Lys Val Leu Gly Tyr Asp Pro Tyr Ile
                165                 170                 175

Gln Pro Glu Ile Val Glu Asn Val Asp Leu Asp Thr Leu Ile Thr Gln
            180                 185                 190

Ala Asp Ile Ile Ser Ile His Cys Pro Leu Thr Arg Glu Asn Phe His
        195                 200                 205

Met Phe Asn Glu Glu Thr Phe Lys Arg Met Lys Pro Gly Ala Ile Leu
    210                 215                 220

Val Asn Thr Ala Arg Gly Gly Leu Ile Asp Thr Lys Ala Leu Leu Glu
225                 230                 235                 240
```

```
Ala Leu Lys Ser Gly Lys Leu Gly Gly Ala Ala Leu Asp Val Tyr Glu
            245                 250                 255

Tyr Glu Arg Gly Leu Phe Phe Lys Asn His Gln Lys Glu Gly Ile Lys
        260                 265                 270

Asp Pro Tyr Leu Ala Gln Leu Leu Gly Leu Ala Asn Val Val Leu Thr
            275                 280                 285

Gly His Gln Ala Phe Leu Thr Arg Glu Ala Val Lys Asn Ile Glu Glu
        290                 295                 300

Thr Thr Val Glu Asn Ile Leu Glu Trp Gln Lys Asn Pro Gln Ala Lys
305                 310                 315                 320

Leu Lys Asn Glu Ile
            325

<210> SEQ ID NO 2
<211> LENGTH: 978
<212> TYPE: DNA
<213> ORGANISM: Thermodesulfatator indicus DSM 15286

<400> SEQUENCE: 2
atgaaagtaa ttttttttag tatgcacccg tatgaagagg aattttttagg gcctatttta    60 ccttctgact gggacgtaga atgacgcct gactttttag acgaaaccac ggtgaaaag    120 gctaaaggag cccaggtagt aagcttgttt gtttcggaca agctgatgg tcccgtactt    180 gaagcgctac attcttacgg agtgggcctt ttggcccttc gtagtgctgg ctatgatcac    240
atagatattg agaccgcaaa acgcctgggt ataaaagtag ttaatgtgcc agcctattct    300
ccccacgcta tcgctgacca tactttagct ataatgcttg ctcttattcg tcgtcttcac    360
cgggcccatg ataaagtgcg cctgggagat tttgatctcg atggtcttat gggctttgat    420
ttaaatggca agttgctgg tgtaattggg ctagggaaaa taggtcgcct ggtagctacc    480
cgcttaaaag cgtttggttg caaagtttta ggctatgatc catacattca gccggaaata    540
gtagaaaatg ttgatttgga tacccttatc actcaggctg atatcatttc tattcattgt    600
cctcttacgc gagaaaattt tcatatgttt aatgaagaga cttttaagcg gatgaaaccc    660
ggggctattt tggttaacac ggcgcgagga ggtcttatag ataccaaggc cttgcttgag    720
gccttaaagt ctggaaaact tggcggcgca gcccttgatg tgtatgaata tgaacggggc    780
ctctttttta aaaaccacca aaagaaggt ataaaagacc cttatcttgc ccagcttttg    840
gggttggcca atgtagtgtt aaccgggcat caggcctttc ttacgcgaga ggctgtaaaa    900
aacatagaag aaactaccgt agaaaatatt ttagaatggc aaaagaatcc ccaggcaaag    960
cttaaaaatg aaatctga                                                 978

<210> SEQ ID NO 3
<211> LENGTH: 978
<212> TYPE: DNA
<213> ORGANISM: Artificial Sequence
<220> FEATURE:
<223> OTHER INFORMATION: D-lactate Dehydrogenase Gene Codon Optimization

<400> SEQUENCE: 3
atgaaagtaa tttttttttc tatgcacccg tatgaagagg aatttctggg tccgattctg    60
ccgtctgact gggacgtaga atgaccccg gactttctgg acgaaaccac cgtggaaaag    120
gctaaaggtg cccaggtagt aagcctgttt gttctgaca agctgatgg tccggtactg    180 gaagcgctgc attcttacgg tgtgggcctg ctggccctgc gttctgctgg ctatgatcac    240
atcgatattg agaccgcaaa acgcctgggt atcaaagtag ttaacgtgcc agcctattct    300
```

```
ccgcacgcta tcgctgacca tactctggct atcatgctgg ctctgattcg tcgtctgcac    360
cgtgcccatg ataaagtgcg cctgggtgat tttgatctgg atggtctgat gggctttgat    420
ctgaacggca agttgctgg tgtaattggt ctgggtaaaa tcggtcgcct ggtagctacc     480
cgcctgaaag cgtttggttg caaagttctg ggctatgatc catacattca gccggaaatc    540
gtagaaaacg ttgatctgga taccctgatc actcaggctg atatcatttc tattcattgt    600
ccgctgaccc gtgaaaactt tcatatgttt aacgaagaga cttttaagcg tatgaaaccg    660
ggtgctattc tggttaacac cgcgcgtggt ggtctgatcg ataccaaggc cctgctggag    720
gccctgaagt ctggtaaact gggcggcgca gccctggatg tgtatgaata tgaacgtggc    780 ctgttttta aaaaccacca aaagaaggt atcaaagacc cgtatctggc ccagctgctg      840
ggtctggcca acgtagtgct gaccggtcat caggcctttc tgacccgtga ggctgtaaaa    900
aacatcgaag aaactaccgt agaaaacatt ctggaatggc aaaagaaccc gcaggcaaag    960
ctgaaaaacg aaatctaa                                                  978
```

<210> SEQ ID NO 4
<211> LENGTH: 28
<212> TYPE: DNA
<213> ORGANISM: Artificial Sequence
<220> FEATURE:
<223> OTHER INFORMATION: D-lactate dehydrogenase Ldh primer

<400> SEQUENCE: 4

```
ccgcggatcc gatgaaagta attttttt                                       28
```

<210> SEQ ID NO 5
<211> LENGTH: 46
<212> TYPE: DNA
<213> ORGANISM: Artificial Sequence
<220> FEATURE:
<223> OTHER INFORMATION: D-lactate dehydrogenase Ldh primer

<400> SEQUENCE: 5

```
tcttcatacg ggtgcataga aaaaaaaatt actttcatcg gatccg                   46
```

<210> SEQ ID NO 6
<211> LENGTH: 45
<212> TYPE: DNA
<213> ORGANISM: Artificial Sequence
<220> FEATURE:
<223> OTHER INFORMATION: D-lactate dehydrogenase Ldh primer

<400> SEQUENCE: 6

```
ttctatgcac ccgtatgaag aggaatttct gggtccgatt ctgcc                    45
```

<210> SEQ ID NO 7
<211> LENGTH: 45
<212> TYPE: DNA
<213> ORGANISM: Artificial Sequence
<220> FEATURE:
<223> OTHER INFORMATION: D-lactate dehydrogenase Ldh primer

<400> SEQUENCE: 7

```
ggggtcattt ctacgtccca gtcagacggc agaatcggac ccaga                    45
```

<210> SEQ ID NO 8
<211> LENGTH: 45
<212> TYPE: DNA
<213> ORGANISM: Artificial Sequence
<220> FEATURE:

<223> OTHER INFORMATION: D-lactate dehydrogenase Ldh primer

<400> SEQUENCE: 8
gggacgtaga aatgaccccg gactttctgg acgaaaccac cgtgg                45

<210> SEQ ID NO 9
<211> LENGTH: 45
<212> TYPE: DNA
<213> ORGANISM: Artificial Sequence
<220> FEATURE:
<223> OTHER INFORMATION: D-lactate dehydrogenase Ldh primer

<400> SEQUENCE: 9
cttactacct gggcaccttt agccttttcc acggtggttt cgtcc                45

<210> SEQ ID NO 10
<211> LENGTH: 45
<212> TYPE: DNA
<213> ORGANISM: Artificial Sequence
<220> FEATURE:
<223> OTHER INFORMATION: D-lactate dehydrogenase Ldh primer

<400> SEQUENCE: 10
taaaggtgcc caggtagtaa gcctgtttgt ttctgacaaa gctga                45

<210> SEQ ID NO 11
<211> LENGTH: 45
<212> TYPE: DNA
<213> ORGANISM: Artificial Sequence
<220> FEATURE:
<223> OTHER INFORMATION: D-lactate dehydrogenase Ldh primer

<400> SEQUENCE: 11
gcagcgcttc cagtaccgga ccatcagctt tgtcagaaac aaaca                45

<210> SEQ ID NO 12
<211> LENGTH: 45
<212> TYPE: DNA
<213> ORGANISM: Artificial Sequence
<220> FEATURE:
<223> OTHER INFORMATION: D-lactate dehydrogenase Ldh primer

<400> SEQUENCE: 12
ggtactggaa gcgctgcatt cttacggtgt gggcctgctg gccct                45

<210> SEQ ID NO 13
<211> LENGTH: 45
<212> TYPE: DNA
<213> ORGANISM: Artificial Sequence
<220> FEATURE:
<223> OTHER INFORMATION: D-lactate dehydrogenase Ldh primer

<400> SEQUENCE: 13
aatatcgatg tgatcatagc cagcagaacg cagggccagc aggcc                45

<210> SEQ ID NO 14
<211> LENGTH: 45
<212> TYPE: DNA
<213> ORGANISM: Artificial Sequence
<220> FEATURE:
<223> OTHER INFORMATION: D-lactate dehydrogenase Ldh primer

<400> SEQUENCE: 14
ctggctatga tcacatcgat attgagaccg caaaacgcct gggta                45

<210> SEQ ID NO 15
<211> LENGTH: 45
<212> TYPE: DNA
<213> ORGANISM: Artificial Sequence
<220> FEATURE:
<223> OTHER INFORMATION: D-lactate dehydrogenase Ldh primer

<400> SEQUENCE: 15
gaataggctg gcacgttaac tactttgata cccaggcgtt ttgcg         45

<210> SEQ ID NO 16
<211> LENGTH: 45
<212> TYPE: DNA
<213> ORGANISM: Artificial Sequence
<220> FEATURE:
<223> OTHER INFORMATION: D-lactate dehydrogenase Ldh primer

<400> SEQUENCE: 16
agttaacgtg ccagcctatt ctccgcacgc tatcgctgac catac         45

<210> SEQ ID NO 17
<211> LENGTH: 45
<212> TYPE: DNA
<213> ORGANISM: Artificial Sequence
<220> FEATURE:
<223> OTHER INFORMATION: D-lactate dehydrogenase Ldh primer

<400> SEQUENCE: 17
aatcagagcc agcatgatag ccagagtatg gtcagcgata gcgtg         45

<210> SEQ ID NO 18
<211> LENGTH: 45
<212> TYPE: DNA
<213> ORGANISM: Artificial Sequence
<220> FEATURE:
<223> OTHER INFORMATION: D-lactate dehydrogenase Ldh primer

<400> SEQUENCE: 18
gctatcatgc tggctctgat tcgtcgtctg caccgtgccc atgat         45

<210> SEQ ID NO 19
<211> LENGTH: 45
<212> TYPE: DNA
<213> ORGANISM: Artificial Sequence
<220> FEATURE:
<223> OTHER INFORMATION: D-lactate dehydrogenase Ldh primer

<400> SEQUENCE: 19
ccagatcaaa atcacccagg cgcactttat catgggcacg gtgca         45

<210> SEQ ID NO 20
<211> LENGTH: 45
<212> TYPE: DNA
<213> ORGANISM: Artificial Sequence
<220> FEATURE:
<223> OTHER INFORMATION: D-lactate dehydrogenase Ldh primer

<400> SEQUENCE: 20
cctgggtgat tttgatctgg atggtctgat gggctttgat ctgaa         45

<210> SEQ ID NO 21
<211> LENGTH: 45
<212> TYPE: DNA
<213> ORGANISM: Artificial Sequence
<220> FEATURE:
<223> OTHER INFORMATION: D-lactate dehydrogenase Ldh primer

<400> SEQUENCE: 21
ccaattacac cagcaactttt gccgttcaga tcaaagccca tcaga         45

<210> SEQ ID NO 22
<211> LENGTH: 45
<212> TYPE: DNA
<213> ORGANISM: Artificial Sequence
<220> FEATURE:
<223> OTHER INFORMATION: D-lactate dehydrogenase Ldh primer

<400> SEQUENCE: 22
gcaaagttgc tggtgtaatt ggtctgggta aaatcggtcg cctgg          45

<210> SEQ ID NO 23
<211> LENGTH: 45
<212> TYPE: DNA
<213> ORGANISM: Artificial Sequence
<220> FEATURE:
<223> OTHER INFORMATION: D-lactate dehydrogenase Ldh primer

<400> SEQUENCE: 23
accaaacgct ttcaggcggg tagctaccag gcgaccgatt ttacc          45

<210> SEQ ID NO 24
<211> LENGTH: 45
<212> TYPE: DNA
<213> ORGANISM: Artificial Sequence
<220> FEATURE:
<223> OTHER INFORMATION: D-lactate dehydrogenase Ldh primer

<400> SEQUENCE: 24
cgcctgaaag cgtttggttg caaagttctg ggctatgatc catac          45

<210> SEQ ID NO 25
<211> LENGTH: 45
<212> TYPE: DNA
<213> ORGANISM: Artificial Sequence
<220> FEATURE:
<223> OTHER INFORMATION: D-lactate dehydrogenase Ldh primer

<400> SEQUENCE: 25
ttttctacga tttccggctg aatgtatgga tcatagccca gaact          45

<210> SEQ ID NO 26
<211> LENGTH: 45
<212> TYPE: DNA
<213> ORGANISM: Artificial Sequence
<220> FEATURE:
<223> OTHER INFORMATION: D-lactate dehydrogenase Ldh primer

<400> SEQUENCE: 26
tcagccggaa atcgtagaaa acgttgatct ggataccctg atcac          45

<210> SEQ ID NO 27
<211> LENGTH: 47
<212> TYPE: DNA
<213> ORGANISM: Artificial Sequence
<220> FEATURE:
<223> OTHER INFORMATION: D-lactate dehydrogenase Ldh primer

<400> SEQUENCE: 27
atgaatagaa atgatatcag cctgagtgat cagggtatcc agatcaa        47

<210> SEQ ID NO 28
<211> LENGTH: 45

```
<212> TYPE: DNA
<213> ORGANISM: Artificial Sequence
<220> FEATURE:
<223> OTHER INFORMATION: D-lactate dehydrogenase Ldh primer

<400> SEQUENCE: 28
tcaggctgat atcatttcta ttcattgtcc gctgacccgt gaaaa              45

<210> SEQ ID NO 29
<211> LENGTH: 45
<212> TYPE: DNA
<213> ORGANISM: Artificial Sequence
<220> FEATURE:
<223> OTHER INFORMATION: D-lactate dehydrogenase Ldh primer

<400> SEQUENCE: 29
aaagtctctt cgttaaacat atgaaagttt tcacgggtca gcgga              45

<210> SEQ ID NO 30
<211> LENGTH: 47
<212> TYPE: DNA
<213> ORGANISM: Artificial Sequence
<220> FEATURE:
<223> OTHER INFORMATION: D-lactate dehydrogenase Ldh primer

<400> SEQUENCE: 30
ctttcatatg tttaacgaag agactttaa gcgtatgaaa ccgggtg              47

<210> SEQ ID NO 31
<211> LENGTH: 45
<212> TYPE: DNA
<213> ORGANISM: Artificial Sequence
<220> FEATURE:
<223> OTHER INFORMATION: D-lactate dehydrogenase Ldh primer

<400> SEQUENCE: 31
ccacgcgcgg tgttaaccag aatagcaccc ggtttcatac gctta              45

<210> SEQ ID NO 32
<211> LENGTH: 45
<212> TYPE: DNA
<213> ORGANISM: Artificial Sequence
<220> FEATURE:
<223> OTHER INFORMATION: D-lactate dehydrogenase Ldh primer

<400> SEQUENCE: 32
gttaacaccg cgcgtggtgg tctgatcgat accaaggccc tgctg              45

<210> SEQ ID NO 33
<211> LENGTH: 45
<212> TYPE: DNA
<213> ORGANISM: Artificial Sequence
<220> FEATURE:
<223> OTHER INFORMATION: D-lactate dehydrogenase Ldh primer

<400> SEQUENCE: 33
gcccagttta ccagacttca gggcctccag cagggccttg gtatc              45

<210> SEQ ID NO 34
<211> LENGTH: 45
<212> TYPE: DNA
<213> ORGANISM: Artificial Sequence
<220> FEATURE:
<223> OTHER INFORMATION: D-lactate dehydrogenase Ldh primer

<400> SEQUENCE: 34
```
ctgaagtctg gtaaactggg cggcgcagcc ctggatgtgt atgaa                45

<210> SEQ ID NO 35
<211> LENGTH: 45
<212> TYPE: DNA
<213> ORGANISM: Artificial Sequence
<220> FEATURE:
<223> OTHER INFORMATION: D-lactate dehydrogenase Ldh primer

<400> SEQUENCE: 35
ttttaaaaaa caggccacgt tcatattcat acacatccag ggctg                45

<210> SEQ ID NO 36
<211> LENGTH: 45
<212> TYPE: DNA
<213> ORGANISM: Artificial Sequence
<220> FEATURE:
<223> OTHER INFORMATION: D-lactate dehydrogenase Ldh primer

<400> SEQUENCE: 36
gaacgtggcc tgttttttaa aaaccaccaa aaagaaggta tcaaa                45

<210> SEQ ID NO 37
<211> LENGTH: 45
<212> TYPE: DNA
<213> ORGANISM: Artificial Sequence
<220> FEATURE:
<223> OTHER INFORMATION: D-lactate dehydrogenase Ldh primer

<400> SEQUENCE: 37
gcagctgggc cagatacggg tctttgatac cttcttttg gtggt                 45

<210> SEQ ID NO 38
<211> LENGTH: 45
<212> TYPE: DNA
<213> ORGANISM: Artificial Sequence
<220> FEATURE:
<223> OTHER INFORMATION: D-lactate dehydrogenase Ldh primer

<400> SEQUENCE: 38
cgtatctggc ccagctgctg ggtctggcca acgtagtgct gaccg                45

<210> SEQ ID NO 39
<211> LENGTH: 45
<212> TYPE: DNA
<213> ORGANISM: Artificial Sequence
<220> FEATURE:
<223> OTHER INFORMATION: D-lactate dehydrogenase Ldh primer

<400> SEQUENCE: 39
cctcacgggt cagaaaggcc tgatgaccgg tcagcactac gttgg                45

<210> SEQ ID NO 40
<211> LENGTH: 45
<212> TYPE: DNA
<213> ORGANISM: Artificial Sequence
<220> FEATURE:
<223> OTHER INFORMATION: D-lactate dehydrogenase Ldh primer

<400> SEQUENCE: 40
cctttctgac ccgtgaggct gtaaaaaaca tcgaagaaac taccg                45

<210> SEQ ID NO 41
<211> LENGTH: 48
<212> TYPE: DNA
<213> ORGANISM: Artificial Sequence
<220> FEATURE:
<223> OTHER INFORMATION: D-lactate dehydrogenase Ldh primer

<400> SEQUENCE: 41
ttgccattcc agaatgtttt ctacggtagt ttcttcgatg ttttttac                    48

<210> SEQ ID NO 42
<211> LENGTH: 45
<212> TYPE: DNA
<213> ORGANISM: Artificial Sequence
<220> FEATURE:
<223> OTHER INFORMATION: D-lactate dehydrogenase Ldh primer

<400> SEQUENCE: 42
tagaaaacat tctggaatgg caaaagaacc cgcaggcaaa gctga                       45

<210> SEQ ID NO 43
<211> LENGTH: 40
<212> TYPE: DNA
<213> ORGANISM: Artificial Sequence
<220> FEATURE:
<223> OTHER INFORMATION: D-lactate dehydrogenase Ldh primer

<400> SEQUENCE: 43
gcccaagctt ttagatttcg tttttcagct ttgcctgcgg                             40

<210> SEQ ID NO 44
<211> LENGTH: 32
<212> TYPE: DNA
<213> ORGANISM: Artificial Sequence
<220> FEATURE:
<223> OTHER INFORMATION: ldh-up-F

<400> SEQUENCE: 44
tacgggatcc tcggcgaccg atgaaccgaa ct                                     32

<210> SEQ ID NO 45
<211> LENGTH: 30
<212> TYPE: DNA
<213> ORGANISM: Artificial Sequence
<220> FEATURE:
<223> OTHER INFORMATION: ldh-up-R

<400> SEQUENCE: 45
tccgctcgag gactcatcat tcctttgccg                                        30

<210> SEQ ID NO 46
<211> LENGTH: 29
<212> TYPE: DNA
<213> ORGANISM: Artificial Sequence
<220> FEATURE:
<223> OTHER INFORMATION: ldh-Dn-F

<400> SEQUENCE: 46
ccgctcgagg gcgtaactga acaccatga                                         29

<210> SEQ ID NO 47
<211> LENGTH: 31
<212> TYPE: DNA
<213> ORGANISM: Artificial Sequence
<220> FEATURE:
<223> OTHER INFORMATION: ldh-Dn-R

<400> SEQUENCE: 47
catgccatgg caaagaaagc gatgaccggc a                                      31

```
<210> SEQ ID NO 48
<211> LENGTH: 32
<212> TYPE: DNA
<213> ORGANISM: Artificial Sequence
<220> FEATURE:
<223> OTHER INFORMATION: Als1-up-F

<400> SEQUENCE: 48
acgcggatcc ctttggcaat gacgatcagc ga                                32

<210> SEQ ID NO 49
<211> LENGTH: 48
<212> TYPE: DNA
<213> ORGANISM: Artificial Sequence
<220> FEATURE:
<223> OTHER INFORMATION: Als1-up-R

<400> SEQUENCE: 49
tgcatagaaa aaaaattac tttcatagcc ctcactcctc cattttca                48

<210> SEQ ID NO 50
<211> LENGTH: 28
<212> TYPE: DNA
<213> ORGANISM: Artificial Sequence
<220> FEATURE:
<223> OTHER INFORMATION: Als-Dn-F

<400> SEQUENCE: 50
atgaaaaagc cctctttgaa aaggggc                                      28

<210> SEQ ID NO 51
<211> LENGTH: 32
<212> TYPE: DNA
<213> ORGANISM: Artificial Sequence
<220> FEATURE:
<223> OTHER INFORMATION: Als1-Dn-R

<400> SEQUENCE: 51
catgccatgg ggtttcataa gaccgctgat ga                                32

<210> SEQ ID NO 52
<211> LENGTH: 20
<212> TYPE: DNA
<213> ORGANISM: Artificial Sequence
<220> FEATURE:
<223> OTHER INFORMATION: Als1-ldh-F

<400> SEQUENCE: 52
atgaaagtaa ttttttttttc                                             20

<210> SEQ ID NO 53
<211> LENGTH: 46
<212> TYPE: DNA
<213> ORGANISM: Artificial Sequence
<220> FEATURE:
<223> OTHER INFORMATION: Als-ldh-R

<400> SEQUENCE: 53 cccctttttca aagagggctt ttcatttag atttcgtttt tcagct                 46

<210> SEQ ID NO 54
<211> LENGTH: 32
<212> TYPE: DNA
<213> ORGANISM: Artificial Sequence
<220> FEATURE:
<223> OTHER INFORMATION: Als2-up-F
```

<400> SEQUENCE: 54
acgcggatcc gcaaacagct gttcatgaac cg                                     32

<210> SEQ ID NO 55
<211> LENGTH: 48
<212> TYPE: DNA
<213> ORGANISM: Artificial Sequence
<220> FEATURE:
<223> OTHER INFORMATION: Als2-up-R

<400> SEQUENCE: 55
aacgcgctgt tgttcttgta tcggcacggg tacatttgaa ggatcttg                    48

<210> SEQ ID NO 56
<211> LENGTH: 32
<212> TYPE: DNA
<213> ORGANISM: Artificial Sequence
<220> FEATURE:
<223> OTHER INFORMATION: Als2-Dn-R

<400> SEQUENCE: 56
tcccccgggg ggtttcataa gaccgctgat ga                                     32

<210> SEQ ID NO 57
<211> LENGTH: 21
<212> TYPE: DNA
<213> ORGANISM: Artificial Sequence
<220> FEATURE:
<223> OTHER INFORMATION: Als2-Pc-F

<400> SEQUENCE: 57
tgccgataca agaacaacag c                                                 21

<210> SEQ ID NO 58
<211> LENGTH: 47
<212> TYPE: DNA
<213> ORGANISM: Artificial Sequence
<220> FEATURE:
<223> OTHER INFORMATION: Als2-Pc-R

<400> SEQUENCE: 58
attactttca tagccctcac tcctccacgg gttcgctacc tgcatta                     47

<210> SEQ ID NO 59
<211> LENGTH: 35
<212> TYPE: DNA
<213> ORGANISM: Artificial Sequence
<220> FEATURE:
<223> OTHER INFORMATION: Als2-ldh-F

<400> SEQUENCE: 59
ggaggagtga gggctatgaa agtaattttt ttttc                                  35

<210> SEQ ID NO 60
<211> LENGTH: 48
<212> TYPE: DNA
<213> ORGANISM: Artificial Sequence
<220> FEATURE:
<223> OTHER INFORMATION: Als4-up-R

<400> SEQUENCE: 60
tgccccggcc tgcatgcacg tcgacacggg tacatttgaa ggatcttg                    48

<210> SEQ ID NO 61

<210> SEQ ID NO 61
<211> LENGTH: 20
<212> TYPE: DNA
<213> ORGANISM: Artificial Sequence
<220> FEATURE:
<223> OTHER INFORMATION: Als4-P43-F

<400> SEQUENCE: 61
tgtcgacgtg catgcaggcc                                               20

<210> SEQ ID NO 62
<211> LENGTH: 46
<212> TYPE: DNA
<213> ORGANISM: Artificial Sequence
<220> FEATURE:
<223> OTHER INFORMATION: Als4-P43-R

<400> SEQUENCE: 62
attactttca tagccctcac tcctcctata atggtaccgc tatcac                  46

<210> SEQ ID NO 63
<211> LENGTH: 48
<212> TYPE: DNA
<213> ORGANISM: Artificial Sequence
<220> FEATURE:
<223> OTHER INFORMATION: Als6-up-R

<400> SEQUENCE: 63
tttcttcctt aaatttgtac attttccggg tacatttgaa ggatcttg                48

<210> SEQ ID NO 64
<211> LENGTH: 20
<212> TYPE: DNA
<213> ORGANISM: Artificial Sequence
<220> FEATURE:
<223> OTHER INFORMATION: Als6-Pldh-F

<400> SEQUENCE: 64
gaaaatgtac aaatttaagg                                               20

<210> SEQ ID NO 65
<211> LENGTH: 46
<212> TYPE: DNA
<213> ORGANISM: Artificial Sequence
<220> FEATURE:
<223> OTHER INFORMATION: Als6-Pldh-R

<400> SEQUENCE: 65
attactttca tagccctcac tcctccgact catcattcct ttgccg                  46

<210> SEQ ID NO 66
<211> LENGTH: 48
<212> TYPE: DNA
<213> ORGANISM: Artificial Sequence
<220> FEATURE:
<223> OTHER INFORMATION: AlsA-up-R

<400> SEQUENCE: 66
tttgtgctat aaacggcgag tttcatagcc ctcactcctc cattttca                48

<210> SEQ ID NO 67
<211> LENGTH: 21
<212> TYPE: DNA
<213> ORGANISM: Artificial Sequence
<220> FEATURE:
<223> OTHER INFORMATION: AlsA-ldhA-F

<400> SEQUENCE: 67

```
atgaaactcg ccgtttatag c                                              21
```

<210> SEQ ID NO 68
<211> LENGTH: 47
<212> TYPE: DNA
<213> ORGANISM: Artificial Sequence
<220> FEATURE:
<223> OTHER INFORMATION: AlsA-ldhA-R

<400> SEQUENCE: 68

```
cccctttca aagagggctt tttcattaa accagttcgt tcgggca                    47
```

<210> SEQ ID NO 69
<211> LENGTH: 300
<212> TYPE: DNA
<213> ORGANISM: Bacillus licheniformis ATCC 14580

<400> SEQUENCE: 69

```
aaggtgacgc ctatttcact ttctagctgt ttaatctgct ggctgagcgg aggctgagtc    60
atgttcagcc gaagagctgc ttttccgaaa tgcagttctt cggcaacaac cataaaataa   120
cgaagatggc gcagctccat taatcactca ttcctttctg aatgcgattt cagtcgtttt   180
acatattaat tgtaagacaa agaagtattg gaaaacaatt tccacaagat gtatatttaa   240
taatacaata attttattaa aaattcattg taaatgaatg aaaatggagg agtgagggct   300
```

<210> SEQ ID NO 70
<211> LENGTH: 225
<212> TYPE: DNA
<213> ORGANISM: Delftia acidovorans C17

<400> SEQUENCE: 70

```
tgccgataca agaacaacag cgcgttgagc gcctgccggt gggtggccgg cgccacttgc    60
ttctcggtgg cgagcatggt cagaaaaccc tcgacttcag cttgccccat ttcgcgcgga   120
tgtcgaaacc caccatggct gcgggccgtc cacaacacaa atgccttggc ccagtagaca   180
taagccttct cggtctgtag gctgtaatgc aggtagcgaa cccgt                   225
```

<210> SEQ ID NO 71
<211> LENGTH: 426
<212> TYPE: DNA
<213> ORGANISM: B. subtilis

<400> SEQUENCE: 71

```
tgtcgacgtg catgcaggcc ggggcatatg ggaaacagcg cggacggagc ggaatttcca    60
atttcatgcc gcagccgcct gcgctgttct catttgcggc ttccttgtag agctcagcat   120
tattgagtgg atgattatat tccttttgat aggtggtatg ttttcgcttg aacttttaaa   180
tacagccatt gaacatacgg ttgatttaat aactgacaaa catcaccctc ttgctaaagc   240
ggccaaggac gctgccgccg gggctgtttg cgttttttacc gtgatttcgt gtatcattgg   300
tttacttatt tttttgccaa agctgtaatg gctgaaaatt cttacattta ttttacattt   360
ttagaaatgg gcgtgaaaaa aagcgcgcga ttatgtaaaa tataaagtga tagcggtacc   420
attata                                                              426
```

<210> SEQ ID NO 72
<211> LENGTH: 301
<212> TYPE: DNA
<213> ORGANISM: Bacillus licheniformis ATCC 14580

<400> SEQUENCE: 72

```
gcgataattg aatcatgctg aagaatagtg gtgttatgag cgctgaaaat gggaaacctt      60
atattgatat aggcccgatg cacttgcaga taaaaccgtc ttttgcaacg cgtttatcaa     120
tttttcttta gacataaggc atattttac cagaaaatgt acaaatttaa ggaagaaata     180
cgtggagaca caaaatagac ataaataaaa ttgaaaaagt atgtgaagta ttgcacaata     240
tgaatgtgaa gaatttcaca aacagcttag tttaaaacaa acggcaaagg aatgatgagt     300
c                                                                    301
```

<210> SEQ ID NO 73
<211> LENGTH: 27
<212> TYPE: DNA
<213> ORGANISM: Artificial Sequence
<220> FEATURE:
<223> OTHER INFORMATION: pflA1-F

<400> SEQUENCE: 73

```
ccggaattca tggaacaatg gaaaggt                                         27
```

<210> SEQ ID NO 74
<211> LENGTH: 29
<212> TYPE: DNA
<213> ORGANISM: Artificial Sequence
<220> FEATURE:
<223> OTHER INFORMATION: pflA1-R

<400> SEQUENCE: 74

```
tcgctcgagt ggaaatgtca aacccatag                                       29
```

<210> SEQ ID NO 75
<211> LENGTH: 28
<212> TYPE: DNA
<213> ORGANISM: Artificial Sequence
<220> FEATURE:
<223> OTHER INFORMATION: pflA2-F

<400> SEQUENCE: 75

```
ccgctcgagg acgatggcca ctgggatc                                        28
```

<210> SEQ ID NO 76
<211> LENGTH: 29
<212> TYPE: DNA
<213> ORGANISM: Artificial Sequence
<220> FEATURE:
<223> OTHER INFORMATION: pflA2-R

<400> SEQUENCE: 76

```
atcggatccc tacatcgatt catggaagg                                       29
```

<210> SEQ ID NO 77
<211> LENGTH: 33
<212> TYPE: DNA
<213> ORGANISM: Artificial Sequence
<220> FEATURE:
<223> OTHER INFORMATION: adhB-up-F

<400> SEQUENCE: 77

```
tacgggatcc gaacgggaat cggcaaaggg att                                  33
```

<210> SEQ ID NO 78
<211> LENGTH: 33
<212> TYPE: DNA
<213> ORGANISM: Artificial Sequence

```
<220> FEATURE:
<223> OTHER INFORMATION: adhB-up-R

<400> SEQUENCE: 78
tccgctcgag cgatgataaa ggctgccgag cta                              33

<210> SEQ ID NO 79
<211> LENGTH: 30
<212> TYPE: DNA
<213> ORGANISM: Artificial Sequence
<220> FEATURE:
<223> OTHER INFORMATION: adhB-dn-F

<400> SEQUENCE: 79
accgctcgag tcgtcacact cccattatcg                                  30

<210> SEQ ID NO 80
<211> LENGTH: 30
<212> TYPE: DNA
<213> ORGANISM: Artificial Sequence
<220> FEATURE:
<223> OTHER INFORMATION: adhB-dn-R

<400> SEQUENCE: 80
catgccatgg cgtcgtattt gccgtcagct                                  30

<210> SEQ ID NO 81
<211> LENGTH: 30
<212> TYPE: DNA
<213> ORGANISM: Artificial Sequence
<220> FEATURE:
<223> OTHER INFORMATION: ack-up-F

<400> SEQUENCE: 81
tacgggatcc gaaggctttc cggccttact                                  30

<210> SEQ ID NO 82
<211> LENGTH: 30
<212> TYPE: DNA
<213> ORGANISM: Artificial Sequence
<220> FEATURE:
<223> OTHER INFORMATION: ack-up-R

<400> SEQUENCE: 82
tccgctcgag catcgtcatt ccgacgaatg                                  30

<210> SEQ ID NO 83
<211> LENGTH: 30
<212> TYPE: DNA
<213> ORGANISM: Artificial Sequence
<220> FEATURE:
<223> OTHER INFORMATION: ack-dn-F

<400> SEQUENCE: 83
accgctcgag gagcttccag cattgattgc                                  30

<210> SEQ ID NO 84
<211> LENGTH: 30
<212> TYPE: DNA
<213> ORGANISM: Artificial Sequence
<220> FEATURE:
<223> OTHER INFORMATION: ack-dn-R

<400> SEQUENCE: 84
catgccatgg atgcggtcat ctgcgatctt                                  30
```

<210> SEQ ID NO 85
<211> LENGTH: 341
<212> TYPE: PRT
<213> ORGANISM: Nostoc sp. PCC 7120

<400> SEQUENCE: 85

Met Lys Val Ala Val Phe Ser Thr Lys Ala Tyr Asp Arg Gln Phe Leu
1               5                   10                  15

Glu Ala Ala Asn Ala Pro Lys His His Glu Leu Ala Phe Phe Glu Pro
            20                  25                  30

Arg Leu Asn Gln Asp Thr Ala Ile Leu Ala Ala Gly Phe Pro Ala Val
        35                  40                  45

Cys Val Phe Val His Asp Gln Val Asp Ala Ala Thr Leu Glu Ile Leu
    50                  55                  60

Ala Ser Arg Gly Thr Arg Leu Ile Val Leu Arg Cys Ala Gly Phe Asn
65                  70                  75                  80

Asn Val Asp Leu Lys Ala Ala Asn Lys Leu Gly Val Thr Val Val Arg
                85                  90                  95

Val Pro Ala Tyr Ser Pro Tyr Gly Val Ala Glu His Ala Val Gly Leu
            100                 105                 110

Ile Leu Ser Leu Asn Arg Lys Ile His Arg Ala Tyr Asn Arg Val Arg
        115                 120                 125

Glu Gly Asn Phe Ala Leu Asp Gly Leu Leu Gly Phe Asn Ile Asn Gly
    130                 135                 140

Arg Thr Val Gly Ile Ile Gly Thr Gly Lys Ile Gly Leu Ile Leu Gly
145                 150                 155                 160

Gln Ile Met Lys Gly Phe Gly Cys Arg Leu Leu Ala Tyr Asp Val Tyr
                165                 170                 175

Arg Asn Pro Glu Met Glu Ser Leu Gly Gly Glu Tyr Val Glu Leu Pro
            180                 185                 190

Glu Leu Phe Ala Asn Ser Asp Ile Ile Ser Leu His Cys Pro Leu Met
        195                 200                 205

Pro Gln Thr His His Leu Ile Asn Ala Glu Ala Ile Glu Gln Val Lys
    210                 215                 220

Pro Gly Val Met Leu Ile Asn Thr Ser Arg Gly Ala Leu Ile His Thr
225                 230                 235                 240

Gln Ala Val Ile Glu Gly Leu Lys Thr Gly Lys Ile Gly Ser Leu Gly
                245                 250                 255

Val Asp Val Tyr Glu Gln Glu Ser Glu Leu Phe Phe Glu Asp Leu Ser
            260                 265                 270

Gly Glu Ile Ile Gln Asp Asp Ile Phe Gln Arg Leu Thr Thr Phe Pro
        275                 280                 285

Asn Val Leu Ile Thr Gly His Gln Ala Phe Phe Thr Glu Asp Ala Leu
    290                 295                 300

Arg Asn Ile Ala Glu Thr Thr Leu Asn Asn Ile Ala Asp Ile Glu Gln
305                 310                 315                 320

Gly Arg Ser Cys Pro Asn Glu Ile Arg Tyr Gln Pro Glu Val Glu Ala
                325                 330                 335

Lys Val Leu Val Ser
            340

<210> SEQ ID NO 86
<211> LENGTH: 329
<212> TYPE: PRT
<213> ORGANISM: Marinomonas sp. MWYL1

<400> SEQUENCE: 86

```
Met Lys Val Ala Val Phe Ser Cys Lys Pro Tyr Asp Lys Arg Thr Leu
1               5                   10                  15

Ser Thr Phe Ala Asp Val Thr Asp Leu Ser Met Ile Tyr Phe Glu Ser
            20                  25                  30

Arg Leu Ser Met Glu Thr Ile Ser Leu Val Lys Gly Phe Asp Ala Val
        35                  40                  45

Ser Cys Phe Val Asn Asp Val Asn Ala Asp Val Ile Gln Cys Leu
    50                  55                  60

Lys Gln Gln Gly Val Lys Thr Ile Ala Leu Arg Cys Ala Gly Phe Asn
65                  70                  75                  80

Asn Val Asp Leu Asp Ala Ala Lys Lys Gln Gly Ile Lys Val Phe His
                85                  90                  95

Val Pro Asp Tyr Ser Pro Thr Ser Val Ala Glu His Ala Val Ala Leu
            100                 105                 110

Ile Met Thr Leu Asn Arg Lys Thr His Arg Ala Tyr His Arg Val Lys
        115                 120                 125

Glu Gly Asn Phe Ala Leu Glu Gly Leu Met Gly Phe Asn Leu Glu Gly
130                 135                 140

Lys Thr Val Gly Cys Ile Gly Thr Gly Arg Ile Gly Ala Ala Phe Cys
145                 150                 155                 160

Arg Ile Met Lys Gly Phe Gly Cys Lys Val Leu Cys Tyr Asp Leu Tyr
                165                 170                 175

Pro Ser Gln Glu Leu Ile Asp Gln Gly Cys Gln Tyr Leu Thr Leu Asp
            180                 185                 190

Glu Ile Tyr Gln Lys Ser Asp Ile Ile Ser Leu His Cys Pro Leu Asn
        195                 200                 205

Thr Ser Thr His His Leu Ile Asn Lys Asp Ser Leu Ala Lys Met Lys
210                 215                 220

Asp Gly Val Met Ile Ile Asn Thr Ser Arg Gly Ala Leu Val His Ala
225                 230                 235                 240

Gln Glu Ala Ile Asp Ala Leu Tyr Ser Gly Lys Ile Gly Tyr Leu Gly
                245                 250                 255

Leu Asp Val Tyr Glu Gln Glu Asn Lys Ile Phe Phe Glu Asp Met Ser
            260                 265                 270

Ser His Ile Ile Gln Asp Ser Val Phe Gln Leu Met Leu Thr Phe Pro
        275                 280                 285

Asn Val Val Val Thr Gly His Gln Gly Tyr Phe Thr Ile Glu Ala Leu
290                 295                 300

Asn His Ile Ala Glu Thr Thr Ile Asp Asn Leu Leu His His Gln Ser
305                 310                 315                 320

Asp Ser Ser Gly Ala Arg Gln Leu Ala
                325

<210> SEQ ID NO 87
<211> LENGTH: 345
<212> TYPE: PRT
<213> ORGANISM: Eubacterium limosum KIST612

<400> SEQUENCE: 87

Met Lys Ile Ala Phe Tyr Asp Thr Arg Pro Tyr Asp Lys Leu Trp Phe
1               5                   10                  15

Asp Pro Leu Leu Lys Asp Ala Gly His Glu Pro Arg Tyr Ile Glu Asn
            20                  25                  30
```

Arg Leu Asp Ile His Thr Leu Glu Tyr Ala Gln Gly Ala Asp Ala Ile
            35                  40                  45

Cys Val Phe Val Asn Asp Lys Val Thr Lys Glu Ile Val Asp Arg Leu
 50                  55                  60

Ser Glu Met Asn Ile His Leu Ile Leu Arg Ser Ala Gly Tyr Asn
 65                  70                  75                  80

Asn Val Asp Met Lys Glu Ala Tyr Gln Lys His Ile Arg Ile Leu Arg
                85                  90                  95

Val Pro Ala Tyr Ser Pro Ala Ala Val Ala Glu Tyr Ala Ala Ser Leu
               100                 105                 110

Leu Leu Ala Val Asn Arg Lys Thr His Lys Ala Tyr Ala Arg Thr Arg
               115                 120                 125

Asp Phe Asn Phe Asn Ile Asp Gly Leu Thr Gly Met Asp Leu Tyr Gly
130                 135                 140

Lys Thr Ala Gly Val Ile Gly Thr Gly Arg Ile Gly Gln Met Met Ile
145                 150                 155                 160

Asp Ile Leu Lys Gly Phe His Met Asn Ile Ile Ala Tyr Asp Val Phe
                165                 170                 175

Pro Asn Ser Lys Leu Asp Ile Gln Tyr Val Pro Leu Glu Glu Leu Met
                180                 185                 190

Glu Lys Ser Asp Ile Ile Ser Leu His Cys Pro Leu Thr Glu Glu Thr
                195                 200                 205

Arg His Ile Ile Asn Asp Gln Thr Ile Gly Met Met Lys Asp Gly Val
                210                 215                 220

Ile Leu Ile Asn Thr Ser Arg Gly Ala Leu Ile Asp Thr Gln Ala Leu
225                 230                 235                 240

Ile Lys Gly Ile Asn Ala His Lys Ile Gly Gly Val Gly Met Asp Val
                245                 250                 255

Tyr Glu Glu Glu Asp Ser Tyr Phe Phe Glu Asp Trp Ser Asp Lys Ile
                260                 265                 270

Met Asp Asp Arg Asp Leu Ala Arg Ile Ile Thr Phe Pro Asn Val Leu
                275                 280                 285

Leu Thr Ser His Gln Ala Phe Leu Thr Thr Glu Ala Leu His Gln Ile
                290                 295                 300

Ala Ala Thr Thr Leu Glu Asn Ile Lys Ala Tyr Glu Asp Asp Val Phe
305                 310                 315                 320

Thr Pro Asn Glu Ile Cys Tyr Gln Cys Glu Lys Gly Asp Cys His
                325                 330                 335

Arg Arg Glu Asn His Gln Lys Cys Phe
                340                 345

<210> SEQ ID NO 88
<211> LENGTH: 421
<212> TYPE: PRT
<213> ORGANISM: Chlamydomonas reinhardtii

<400> SEQUENCE: 88

Met Met Leu Leu Ser Ser Thr Gln Ser His Cys Leu Thr Ala Ser Lys
1               5                   10                  15

Ala Asn Gln Arg Asn Val Val Ala Lys Pro Gly Ile Ile Ala Arg Gly
                20                  25                  30

Arg Gly Leu Val Gln His Arg Ala Tyr Arg Val Ala Ala Leu Asn Val
            35                  40                  45

Gly Pro Gly Gly Gly Ser Pro Val Ser Thr Val Glu Asp Thr Gly Arg

Val Glu Leu Thr Pro Gln Glu Ala Ala Lys Val Ala Thr Thr Arg Cys
65                  70                  75                  80

Ile Cys Tyr Ser Thr Thr Gln Tyr Val Lys Asp Phe Leu Ala Gly Pro
                85                  90                  95

Met Gln Lys Val Phe Thr Asp Thr Tyr Phe Val Glu Pro Pro Leu Asp
            100                 105                 110

Lys Asp Thr Ala Gln Leu Ala Arg Gly Tyr Asp Val Ala Val Leu Phe
            115                 120                 125

Val Asn Asp Arg Ala Asp Ala Ser Val Ile Lys Glu Leu Ala Lys Ala
        130                 135                 140

Gly Val Lys Leu Ile Ala Leu Arg Cys Ala Gly Phe Asp Arg Val Asp
145                 150                 155                 160

Leu His Ala Cys Ala Glu His Gly Val Arg Val Val Arg Val Pro Thr
                165                 170                 175

Tyr Ser Pro Glu Ser Val Ala Glu His Ala Val Ala Leu Ile Phe Ala
            180                 185                 190

Leu Asn Arg His Leu Thr Asp Ala Tyr Ile Arg Val Arg Met Gly Asn
        195                 200                 205

Tyr Ser Leu Ser Gly Leu Val Gly Val Glu Met Arg His Lys Val Val
210                 215                 220

Gly Val Val Gly Thr Gly Ala Ile Gly Gln Gln Ala Ala Arg Ile Leu
225                 230                 235                 240

Lys Gly Ile Gly Cys Lys Val Phe Ala Tyr Asp Ile Lys Pro Asn Pro
                245                 250                 255

Ala Val Glu Ala Met Gly Ile Pro Tyr Val Ser Leu Asp Glu Leu Leu
            260                 265                 270

Ala Met Ser Asp Ile Val Thr Leu His Cys Pro Leu Leu Pro Ser Thr
        275                 280                 285

Arg Gln Leu Ile Asn Lys Glu Ser Ile Gln Lys Met Lys Lys Gly Val
290                 295                 300

Met Leu Ile Asn Val Ser Arg Gly Gly Leu Ile Asp Ser Ala Ala Leu
305                 310                 315                 320

Phe Asp Ala Leu Glu Ser Gly Gln Ile Gly Ala Leu Gly Leu Asp Val
                325                 330                 335

Tyr Glu Asn Glu Gly Gly Leu Phe Phe Val Asp His Thr Lys Phe Asp
            340                 345                 350

Pro Ser Val Arg Met Gln Lys Trp Asp Arg Gln Phe Arg Thr Leu Leu
            355                 360                 365

Ser Tyr Pro Gln Val Leu Val Thr Pro His Thr Ala Phe Leu Thr Glu
        370                 375                 380

Glu Ala Leu Asn Asn Ile Cys Thr Thr Thr Ile Gln Asn Ile Ala Asp
385                 390                 395                 400

Tyr Val Leu Asp Arg Pro Leu Gly Asn Glu Val Lys Ala Gln Pro Ala
                405                 410                 415

Pro Ala Gly Lys Thr
            420

<210> SEQ ID NO 89
<211> LENGTH: 332
<212> TYPE: PRT
<213> ORGANISM: Truepera radiovictrix DSM 17093

<400> SEQUENCE: 89

Met Asp Leu Ala Ile Phe Ser Thr Lys Pro Tyr Asp Arg Arg Phe
1               5                   10                  15

Glu Ala Ala Asn Ala Glu His Gly His Gly Leu His Phe Phe Glu Pro
            20                  25                  30

Arg Leu Thr Pro Glu Thr Ala Ser Leu Ala Ala Gly Phe Thr Gly Val
                35                  40                  45

Cys Ala Phe Val Asn Asp Val Leu Ser Ala Pro Val Leu Arg Glu Leu
50                  55                  60

Ala Ala Gly Gly Thr Lys Leu Ile Ala Leu Arg Ser Ala Gly Phe Asn
65                  70                  75                  80

His Val Asp Leu Gly Ala Ala Gln Glu Leu Gly Leu Thr Val Ala Arg
                85                  90                  95

Val Pro Ala Tyr Ser Pro Tyr Ala Val Ala Glu His Ala Leu Ala Leu
            100                 105                 110

Ile Leu Thr Leu Asn Arg Lys Thr His Arg Ala Phe Asn Arg Val Arg
            115                 120                 125

Glu Gly Asn Phe Ala Leu Asp Gly Leu Leu Gly Phe Asp Leu His Gly
        130                 135                 140

Lys Thr Val Gly Val Val Gly Thr Gly Lys Ile Gly Leu Ile Phe Ala
145                 150                 155                 160

Arg Ile Ala Ala Gly Phe Gly Cys Glu Val Leu Ala Tyr Asp Pro Tyr
                165                 170                 175

Pro Asn Pro Glu Ala Arg Ala Arg Tyr Val Pro Leu Pro Glu Leu Leu
            180                 185                 190

Gly Ala Ala Asp Ile Val Ser Leu His Cys Pro Leu Thr Pro Glu Thr
        195                 200                 205

Tyr His Leu Ile Gly Lys Glu Ala Val Ala Gln Met Lys Pro Gly Ala
        210                 215                 220

Met Leu Ile Asn Thr Ser Arg Gly Ala Leu Val Asp Thr Arg Ala Val
225                 230                 235                 240

Ile His Gly Leu Lys Ser Gly Gln Ile Gly Ala Leu Gly Leu Asp Val
                245                 250                 255

Tyr Glu Glu Glu Ala Asp Leu Phe Phe Glu Asp Leu Ser Asp Arg Val
            260                 265                 270

Ile Gln Asp Asp Val Phe Thr Arg Leu Leu Thr Phe Pro Asn Val Leu
        275                 280                 285

Ile Thr Gly His Gln Gly Phe Phe Thr Val Glu Ala Leu Asp Asn Ile
        290                 295                 300

Ala His Thr Thr Leu Arg Asn Val Thr Ala Phe Glu Thr Gly Ala Gly
305                 310                 315                 320

Glu Leu His Arg Val Ala Val Asp Thr Ala His Ala
                325                 330

<210> SEQ ID NO 90
<211> LENGTH: 333
<212> TYPE: PRT
<213> ORGANISM: Salinispora tropica CNB-440

<400> SEQUENCE: 90

Met Arg Val Ser Val Phe Ser Thr Lys Pro Tyr Asp Arg Glu Phe Leu
1               5                   10                  15

Ser Ala Ala Asn Ser Met Asp Gly His Glu Leu Glu Phe Leu Glu Pro
            20                  25                  30

Arg Leu Thr Pro Gln Thr Ala Lys Leu Ala Ser Gly Ala Ala Ala Val
                35                  40                  45

Cys Ala Phe Val Asn Asp Asp Leu Gly Thr Glu Val Leu Glu Arg Leu
 50                  55                  60

Ala Ala Asp Gly Val Arg Leu Ile Ala Leu Arg Ser Ala Gly Phe Asn
 65                  70                  75                  80

His Val Asp Leu Ala Thr Ala Arg Arg Leu Gly Leu Thr Val Val Arg
                 85                  90                  95

Val Pro Glu Tyr Ser Pro Tyr Ala Val Ala Glu His Thr Val Ala Leu
            100                 105                 110

Met Leu Ala Leu Asn Arg Lys Val Tyr Arg Ala Tyr Asn Arg Val Arg
        115                 120                 125

Glu His Asn Phe Ala Leu Thr Gly Leu Leu Gly Phe Asp Leu His Gly
    130                 135                 140

Arg Thr Val Gly Val Val Gly Thr Gly Lys Ile Gly Phe Cys Val Ala
145                 150                 155                 160

Arg Ile Leu Ser Gly Phe Gly Cys Arg Val Ile Ala Ser Asp Pro Tyr
                165                 170                 175

Pro Asp Asp Ala Val Thr Ala Ala Gly Ile Glu Tyr Val Pro Leu Gln
            180                 185                 190

Arg Leu Leu Ser Glu Ser Asp Val Ile Thr Leu His Cys Pro Leu Thr
        195                 200                 205

Pro Asp Thr Glu His Leu Ile Asn Pro Asp Arg Ile Ala Gln Met Arg
    210                 215                 220

Arg Gly Val Met Leu Ile Asn Thr Ser Arg Gly Ala Leu Val Asp Thr
225                 230                 235                 240

Arg Ala Val Ile Asp Gly Leu Lys Asn Gly Gln Ile Gly Tyr Leu Gly
                245                 250                 255

Leu Asp Val Tyr Glu Glu Glu Thr Asp Leu Phe Phe Glu Asp Leu Ser
            260                 265                 270

Asp Arg Val Leu Asp Asp Asp Phe Ser Arg Leu Asn Thr Phe Pro
        275                 280                 285

Asn Val Leu Ile Thr Gly His Gln Ala Phe Phe Thr Glu Glu Ala Met
    290                 295                 300

Arg Asn Ile Ala Ala Thr Thr Ile Asp Ser Leu Thr Thr Ile Glu Arg
305                 310                 315                 320

Glu Gly Pro Asn Ala Val Pro Gln Ser Ala Arg Val Cys
                325                 330

<210> SEQ ID NO 91
<211> LENGTH: 332
<212> TYPE: PRT
<213> ORGANISM: Schizosaccharomyces pombe

<400> SEQUENCE: 91

Met Arg Ile Ala Phe Phe Ser Ala Gln Pro Tyr Glu Lys Glu Pro Phe
1               5                   10                  15

Glu Lys Val Asn Glu Asn Tyr Lys His Glu Ile Asp Tyr His Glu Ser
            20                  25                  30

Ile Leu Asn Lys Lys Thr Ala Val Leu Ala Glu Lys Ala Pro Val Val
        35                  40                  45

Cys Val Phe Val Asn Asp Lys Val Asp Ala Asp Thr Leu Lys Val Leu
 50                  55                  60

Ala Lys Asn Gly Thr Lys Leu Ile Ala Leu Arg Cys Ala Gly Phe Asn
 65                  70                  75                  80

Asn Val Asp Leu Lys Ala Ala Ala Asp Asn Gly Ile Thr Val Val Arg

```
            85                  90                  95
Val Pro Ala Tyr Ser Pro Tyr Ala Val Ala Glu Tyr Thr Ile Gly Leu
            100                 105                 110

Leu Leu Ser Leu Asn Arg Lys Ile His Arg Ala Tyr Val Arg Val Arg
            115                 120                 125

Glu Asp Asp Phe Asn Leu Asn Gly Leu Leu Gly His Asp Leu His Gly
            130                 135                 140

Lys Thr Ile Gly Leu Leu Gly Thr Gly Arg Ile Gly Gly Leu Val Ala
145                 150                 155                 160

Lys Cys Leu Lys Leu Gly Phe Gly Cys Glu Val Leu Ala His Asp Ile
                165                 170                 175

Lys Pro Asn Lys Glu Leu Glu Lys Phe Gly Ile Gln Phe Val Glu Gln
                180                 185                 190

Gln Glu Val Leu Ala Lys Ala Asp Phe Leu Cys Leu His Cys Pro Leu
                195                 200                 205

Thr Pro Asp Thr Glu His Leu Val Asp Glu Lys Leu Leu Ala Ser Met
            210                 215                 220

Lys Lys Gly Val Lys Ile Ile Asn Thr Ser Arg Gly Gly Leu Val Asp
225                 230                 235                 240

Thr Lys Ala Leu Val Lys Ala Ile Glu Ser Gly Gln Val Gly Gly Cys
                245                 250                 255

Ala Met Asp Val Tyr Glu Gly Glu Arg Arg Leu Phe Tyr Arg Asp Leu
                260                 265                 270

Ser Asn Glu Val Ile Lys Asp Thr Thr Phe Gln Gln Leu Ala Asn Phe
            275                 280                 285

Pro Asn Val Leu Val Thr Ser His Gln Ala Phe Phe Thr Ala Glu Ala
            290                 295                 300

Leu Ser Ala Ile Ala His Thr Thr Leu Lys Asn Val Ser Asp Phe Ala
305                 310                 315                 320

Ser Gln Asn Asn Asp Pro Ser Val Ile Val Lys Asn
                325                 330

<210> SEQ ID NO 92
<211> LENGTH: 334
<212> TYPE: PRT
<213> ORGANISM: Streptomyces albus J1074

<400> SEQUENCE: 92

Met Glu Ile Leu Ala Phe Gly Val Gln Asp Asp Glu Arg Pro Leu Ile
1               5                   10                  15

Glu Arg Ala Phe Ala Gly Glu His Glu Val Arg Cys Val Asp Val Phe
            20                  25                  30

Leu Asn Arg Asp Thr Ala Ala Ile Ala Arg Gly Tyr Glu Ala Ile Ser
        35                  40                  45

Thr Ser Val Asn Ala Asp Leu Gly Gly Pro Val Leu Gln Thr Leu Ala
    50                  55                  60

Ala Gly Gly Thr Gln Phe Ile Ala Gln Arg Ser Thr Gly Phe Asn Asn
65                  70                  75                  80

Ile Asp Leu Asp Val Ala Glu Arg Leu Ala Leu Thr Val Ala Arg Val
                85                  90                  95

Ser Ser Tyr Ser Pro Tyr Ser Val Ala Glu Phe Ala Trp Thr Leu Ala
            100                 105                 110

Met Ala Val Asn Arg Arg Ile Val Arg Ala Ala Asn Arg Thr Arg Asp
        115                 120                 125
```

```
Phe Asp Phe Arg Leu Glu Gly Leu Met Gly Arg Asp Leu Arg Gly Arg
            130                 135                 140
Thr Val Gly Val Ile Gly Thr Gly Arg Ile Gly Glu Ala Phe Thr Arg
145                 150                 155                 160
Ile Ala His Gly Phe Gly Met Asn Leu Leu Gly Trp Asp Ile Ala Glu
                    165                 170                 175
Asn Pro Ala Cys Arg Glu Leu Gly Met Arg Tyr Val Glu Arg Glu Glu
                180                 185                 190
Leu Phe Arg Glu Ala Asp Val Ser Leu His Val Pro Leu Leu Pro
            195                 200                 205
Ala Thr Glu His Leu Val Asp Ala His Ala Leu Asp Leu Met Lys Asp
210                 215                 220
Asp Ala Ile Leu Val Asn Ser Ser Arg Gly Gly Leu Val Asp Thr Arg
225                 230                 235                 240
Ala Leu Val Asp Val Leu Arg Ala Gly Arg Leu Leu Gly Val Gly Leu
                    245                 250                 255
Asp Val Tyr Glu Ala Glu Ala Gly Leu Phe Phe Tyr Asp Lys Ser Leu
                260                 265                 270
Asp Val Val Thr Asp Asp Val Leu Ala Arg Leu Met Thr Phe Pro Asn
            275                 280                 285
Val Val Val Thr Ser His Gln Ala Tyr Tyr Thr Glu Asp Ala Val Thr
        290                 295                 300
Glu Ile Ile Asp Thr Thr Val Arg Asn Val Arg Asp Tyr Val Ala Gly
305                 310                 315                 320
Arg Arg Ser Glu Asn Val Leu Val Pro Ala Leu Pro Pro Arg
                    325                 330

<210> SEQ ID NO 93
<211> LENGTH: 329
<212> TYPE: PRT
<213> ORGANISM: Saccharophagus degradans 2-40

<400> SEQUENCE: 93

Met Lys Ile Gly Leu Phe Ser Ser Lys Tyr Asp Lys Val Val Phe
1               5                   10                  15
His Gln Ile Asn Ser Gly Gln His Glu Ile Thr Tyr His Pro Val Arg
            20                  25                  30
Leu Asn Lys Asp Thr Val Lys Leu Ala Ser Gly Phe Glu Ala Ile Cys
        35                  40                  45
Cys Phe Val Asn Asp Glu Ile Asp Ala Ser Val Ile Ala Ser Leu Ser
    50                  55                  60
Asn Met Asn Val Lys Leu Leu Ala Leu Arg Cys Ala Gly Phe Asn Asn
65                  70                  75                  80
Val Asp Leu Pro Ala Ala Lys Ala Asn Asn Leu Pro Ile Cys Arg Val
                85                  90                  95
Pro Glu Tyr Ser Pro His Ala Val Ala Glu His Thr Cys Ala Leu Ile
            100                 105                 110
Leu Asp Leu Asn Arg Asn Ile His Arg Ala His Asn Arg Ile Arg Glu
        115                 120                 125
Asn Asp Tyr Ser Leu Asp Gly Leu Leu Gly Phe Asp Leu His Gly Lys
    130                 135                 140
Thr Val Gly Val Ile Gly Ala Gly Lys Ile Gly Arg Ala Phe Ile Lys
145                 150                 155                 160
Ile Met Leu Gly Phe Gly Cys Asn Ile Gln Val Cys Asp Pro Asp Tyr
                165                 170                 175
```

```
Ala Gln Pro Asp Asn Pro Lys Ile Lys Lys Gly Asp Leu Asp Asp Val
            180             185             190

Leu Gln Asn Ser Asn Ile Ile Ser Leu His Cys Pro Leu Val Pro Ser
        195             200             205

Thr His His Met Ile Asn Gln Ala Ala Ile Asp Lys Met Lys Pro Gly
    210             215             220

Val Met Leu Ile Asn Thr Ser Arg Gly Gly Leu Val Asp Thr Ser Ala
225             230             235             240

Val Ile Arg Ala Leu Lys Asn Lys Lys Ile Gly His Leu Gly Leu Asp
            245             250             255

Val Tyr Glu Glu Glu Ser Glu Met Phe Phe Glu Asp Phe Ser Asp Thr
        260             265             270

Phe Ile Gln Asp Asp Val Phe Ala Arg Leu Gln Thr Phe Pro Asn Val
        275             280             285

Thr Ile Thr Gly His Gln Ala Phe Phe Thr Lys Glu Ala Leu Glu Lys
    290             295             300

Ile Ala Arg Thr Thr Leu Thr Asn Ile Glu His Phe Gln Arg Gly Glu
305             310             315             320

Phe Asp Lys Val His Phe Val Ser Thr
                325
```

D-LACTATE DEHYDROGENASE, ENGINEERED STRAIN CONTAINING D-LACTATE DEHYDROGENASE AND CONSTRUCTION METHOD AND USE OF ENGINEERED STRAIN

CROSS-REFERENCE TO RELATED APPLICATIONS

This application is the United States national phase of International Application No. PCT/CN2017/072647 filed Jan. 25, 2017, and claims priority to Chinese Patent Application No. 201610056883.7 filed Jan. 27, 2016, the disclosures of which are hereby incorporated in their entirety by reference.

The Sequence Listing associated with this application is filed in electronic format via EFS-Web and is hereby incorporated by reference into the specification in its entirety. The name of the text file containing the Sequence Listing is 1805282_ST25.txt. The size of the text file is 50,426 bytes, and the text file was created on Jul. 25, 2018.

FIELD OF THE INVENTION

The present invention relates to the field of gene engineering, and in particular to a D-lactate dehydrogenase, a construction method of a *Bacillus* gene engineering strain containing the D-lactate dehydrogenase and use of the engineered strain in production of D-lactic acid.

DESCRIPTION OF THE PRIOR ART

Lactic acid is an important industrial raw material and can be applied to pharmaceutical, food, cosmetic and petrochemical industries, etc. In recent years, as a monomer, lactic acid is also used for synthesizing high-strength biodegradable plastic polylactic acid (PLA). Traditionally, PLA is polymerized by using highly optically-pure L-lactic acid. Furthermore, by using mixed L-lactic acid and D-lactic acid, the mechanical performance, heat stability and hydrolysis resistance of products using polylactic acid as materials can be obviously improved, thereby greatly exciting the market demands for D-lactic. Although lactic acid can be synthesized by using petroleum as a raw material, the synthesized lactic acid is a mixture of two types of isomerides and is not applicable to production of PLA. Highly optically-pure L-lactic acid and D-lactic acid needed for producing PLA can only be produced through microbial fermentation, and thus many scholars carry out researches on production of D-lactic acid by using a microbial fermentation method.

High-temperature fermentation can minimize the risk of pollution, improve the conversion rate of raw materials and reduce heat supply cost. Up to now, production of optically-pure L-lactic acid at high temperature has been widely studied, which makes a huge contribution to the commercialized production of L-lactic acid. In regard to D-lactic acid, people always eager to realize high-temperature fermentation production of D-lactic acid. However, there are few reports about thermophilic production of D-lactic acid, and the concentration, production speed and rich culture medium components for reported D-lactic acid are not suitable for industrial production. Therefore, it is very necessary to develop a low-cost strong microbial platform to produce D-lactic acid at high temperature.

D-lactate dehydrogenase on which nicotinamide adenine dinucleotide (NADH) depends is a key enzyme for microbial synthesis of D-lactic acid. However, most natural D-lactate dehydrogenases are not stable to heat, and this is one of major bottlenecks for microbial production of D-lactic acid at high temperature. It is reported that, as proved by in-vitro determination of enzyme activity of D-lactate dehydrogenases in *Lactobacillus plantarum*, this enzyme has very high enzyme activity at 42° C., but is fully deactivated after incubation for 3 min at 50° C., while L-lactate dehydrogenases in *Lactobacillus plantarum* after treatment by using the same process still reserve 94% of enzyme activity. As also shown by other in-vivo experiments, D-lactate dehydrogenases are easily deactivated under a high-temperature condition. On the whole, the low activity or extremely poor heat stability of the D-lactate dehydrogenases reported above prevents the production of D-lactic acid under a high-temperature condition by using the D-lactate dehydrogenases. In order to realize high-efficiency production of D-lactic acid at high temperature, it is an important task to find a D-lactate dehydrogenase having high heat stability.

Heat-resistant *Bacillus licheniformis* ATCC 14580 is a facultative anaerobic, Gram-positive endospore-type bacterium. For a microbial fermentation platform, it has a lot of potential advantages as follows: 1) it can use various pentoses and hexoses; 2) it has a fast cell growth speed and thus can shorten the fermentation period; 3) it can be subjected to genetic operations; and 4) it is a "Generally Recognized as Safe" strain generally accepted by the Food and Drug Administration. These advantages show that strain ATCC 14580 can be used as an ideal platform strain. Up to now, this strain has already been proved to be usable for high-temperature fermentation production of 2,3-butanediol.

Therefore, one skilled in the art devotes himself to developing an engineered strain for D-lactic acid with a high yield at high temperature and preparation and use thereof, by using heat-resistant *Bacillus licheniformis* ATCC 14580 as an original strain.

SUMMARY OF THE INVENTION

With regard to the defects that most natural D-lactate dehydrogenases in the prior art are poor in heat stability, the cost of the existing thermophilic production of D-lactic acid is high and the concentration and production speed of D-lactic acid are not suitable for industrial production, the present invention provides an engineered strain for producing D-lactic acid with a high yield at high temperature, and preparation method and use of the strain. The present invention discloses a D-lactate dehydrogenase which has unique properties and is extracted from *Thermodesulfatator indicus*, and this enzyme has extremely good thermophily and heat stability. After performing codon optimization for the enzyme via colibacillus, by using the optimized enzyme and the gene engineering construction method, a fermentation product of the reconstructed *Bacillus licheniformis* can be redirected to optically-pure D-lactic acid with a high yield from naturally produced 2,3-butanediol.

In one aspect, the present invention provides a D-lactate dehydrogenase. In one specific implementation mode, the D-lactate dehydrogenase has one of the following amino acid sequences:

1) an amino acid sequence expressed by SEQ ID No. 1;
2) an amino acid sequence derivatively produced from the amino acid sequence expressed by SEQ ID No. 1 through substitution, deletion, insertion or addition of one or more amino acid residues, and a protein produced by the amino acid sequence having D-lactate dehydrogenase activity;

3) an amino acid sequence produced from the amino acid sequence expressed by SEQ ID No. 1 through conservative replacement; and 4) an amino acid sequence having at least 80% of homology with the amino acid sequence expressed by SEQ ID No. 1.

Further, the substitution, deletion, insertion or addition of the amino acid residues occurs outside a functional domain comprising enzyme catalytic sites, ligand binding sites and NAD binding sites of the D-lactate dehydrogenase.

Further, according to relative positions, key amino acids at the enzyme catalytic sites are Arg at position 229, Glu at position 258 and His at position 290; key amino acids at the ligand binding sites are Ser, Ala and Gly positions 75-77, Tyr at position 99, Arg at position 229, His at position 290 and Phe at position 293; and key amino acids at the NAD binding sites are Tyr at position 99, Ile at position 104, Gly at position 150, Gly, Lys, Ile and Gly at positions 152-155, Tyr, Asp and Pro at positions 172-174, His, Cys, Pro and Leu at positions 199-202, Asn at position 206, Met at position 209, Thr, Ala and Arg at positions 227-229, Asp and Val at positions 253 and 254, His at position 290, and Ala and Phe at positions 292 and 293.

In another aspect, the present invention provides a nucleotide sequence. In one specific implementation mode, the nucleotide sequence codes the D-lactate dehydrogenase according to claim 1.

Further, the nucleotide sequence is one of the following nucleotide sequences:

1) a nucleotide sequence expressed by SEQ ID No. 2;
2) a nucleotide sequence expressed by SEQ ID No. 3;
3) a nucleotide sequence having more than 80% of homology with the nucleotide sequence expressed by SEQ ID No. 2 or SEQ ID No. 3; and
4) a nucleotide sequence hybridized with a complementary chain of the nucleotide sequence expressed by SEQ ID No. 2 or SEQ ID No. 3 under a high-stringency condition.

In another aspect, the present invention provides use of the D-lactate dehydrogenase as described above or the nucleotide sequence as described above in production of D-lactic acid.

In another aspect, the present invention provides a gene engineering strain. In one specific implementation mode, the gene engineering strain has the D-lactate dehydrogenase as described above or a D-lactate dehydrogenase coded by the nucleotide sequence as described above.

Further, in the gene engineering strain, a pathway for synthesizing L-lactic acid by pyruvic acid is blocked and a pathway for synthesizing 2,3-butanediol by pyruvic acid is blocked.

Preferably, the pathway for synthesizing L-lactic acid by pyruvic acid is blocked by deactivating or deleting an L-lactate dehydrogenase gene; and the pathway for synthesizing 2,3-butanediol by pyruvic acid is blocked by deactivating or deleting one or both of an acetolactate synthase gene and an acetolactate decarboxylase gene.

Preferably, in the gene engineering strain, one or more of a pathway for synthesizing formic acid by pyruvic acid, a pathway for synthesizing acetic acid by pyruvic acid, and a pathway for synthesizing ethanol by pyruvic acid are blocked.

Preferably, the pathway for synthesizing formic acid by pyruvic acid is blocked by deactivating or deleting one or both of a pyruvate formate-lyase gene and a pyruvate formate-lyase activating enzyme gene; the pathway for synthesizing acetic acid by pyruvic acid is blocked by deactivating or deleting one or both of a pyruvate dehydrogenase gene and an acetokinase gene; and the pathway for synthesizing ethanol by pyruvic acid is blocked by deactivating or deleting one or both of a pyruvate dehydrogenase gene and an ethanol dehydrogenase gene.

Preferably, an original D-lactate dehydrogenase gene in the gene engineering strain is deactivated or deleted.

Further, an original strain of the gene engineering strain is *Thermophilus*.

Further, an original strain of the gene engineering strain is *Bacillus*.

Preferably, the *Bacillus* is selected from a group consisting of *Bacillus licheniformis*, *Bacillus coagulans*, *B. subtilis*, *Bacillus amyloliquefaciens*, *Bacillus pumilus*, *Bacillus circulans* and *Aneurinibacillus aneurinilyticus*.

Preferably, a restrictive modification system in the original strain is deactivated or knocked out.

Preferably, the original strain is a ΔhsdR1ΔhsdR2 double-mutant strain MW3 of *Bacillus licheniformis* ATCC 14580.

Further, a promoter of a coding gene of the above D-lactate dehydrogenase is reconstructed into a constitutive promoter.

Preferably, the constitutive promoter is a promoter $P_{als}$ of α-acetolactate synthase of *Bacillus licheniformis* ATCC 14580, a $P_c$ promoter in plasmid pMMPc, a $P_{43}$ promoter in *B. subtilis* or a promoter $P_{ldh}$ of L-lactate dehydrogenase of *Bacillus licheniformis* ATCC 14580.

More preferably, the constitutive promoter is a promoter $P_{als}$ of α-acetolactate synthase of *Bacillus licheniformis* ATCC 14580.

Further, the gene engineering strain is *Bacillus licheniformis* BN11, the preservation number of which is CCTCC NO: M2016026 and which was preserved in China Center for Type Culture Collection on Jan. 8, 2016. *Bacillus licheniformis* BN11 was deposited on Jan. 8, 2016 under the Budapest Treaty with the China Center for Type Culture Collection at Wuhan University, Wuhan 430072, P.R. China, under accession CCTCC M 2016026.

In another aspect, the present invention provides a method for preparing the gene engineering strain as described above. In one specific implementation mode, the method comprises: deactivating or deleting an L-lactate dehydrogenase gene in an original strain; and introducing the nucleotide sequence of the D-lactate dehydrogenase as described above.

Further, the method further comprises: deactivating or deleting an original D-lactate dehydrogenase gene in the original strain; and blocking a pathway for synthesizing 2,3-butanediol by pyruvic acid.

Further, the method further comprises: reconstructing a promoter of the introduced nucleotide sequence into a constitutive promoter.

Further, the original strain is a ΔhsdR1ΔhsdR2 double-mutant strain MW3 of *Bacillus licheniformis* ATCC 14580; and α-acetolactate decarboxylase (alsD) and acetolactate synthase (alsS) genes are replaced with the nucleotide sequence as described above.

In still another aspect, the present invention further provides use of the above gene engineering strain, in particular use in production of D-lactic acid.

In one specific implementation mode, a carbon source adopted in the production is one or more selected from a group consisting of glucose, xylose, maltose, lactose and sucrose.

Preferably, low-price culture mediums containing peanut meal or dried corn steep liquor powder are adopted for fermentation in the production.

Preferably, fermentation temperature for the production is 45° C.-55° C.

Preferably, pH of the fermentation culture mediums in the production is 6.0-8.0.

Preferably, a fermentation process in the production is a continuous fermentation or fed-batch process.

In another aspect, the present invention provides a D-lactate dehydrogenase. In one specific implementation mode, the D-lactate dehydrogenase has one of the following amino acid sequences:

1) an amino acid sequence expressed by SEQ ID No. 1;

2) an amino acid sequence of a derivative protein produced from the amino acid sequence expressed by SEQ ID No. 1 through substitution, deletion or insertion of one or more amino acid residues, the derivative protein having D-lactate dehydrogenase activity; and 3) an amino acid sequence having at least about 80% of homology with the amino acid sequence expressed by SEQ ID No. 1.

The protein comes from *T. indicus*. The above protein may be artificially synthesized and may also be obtained by firstly synthesizing a coding gene thereof and then performing biological expression.

The present invention further provides nucleic acid molecules coding the above D-lactate dehydrogenase, and these nucleic acid molecules may be DNA such as cDNA, genome DNA or recombinant DNA; and may also be RNA such as mRNA, hnRNA or tRNA.

Further, the present invention provides a nucleotide sequence coding the above D-lactate dehydrogenase. The nucleotide sequence is one of the following nucleotide sequences:

1) a nucleotide sequence expressed by SEQ ID No. 2;

2) a nucleotide sequence expressed by SEQ ID No. 3; and 3) a nucleotide sequence having more than 80% of homology with the nucleotide sequence expressed by SEQ ID No. 2 or SEQ ID No. 3.

In another aspect, the present invention provides use of the above D-lactate dehydrogenase or the above nucleotide sequence in production of D-lactic acid.

In another aspect, the present invention provides a gene engineering strain, characterized in that the gene engineering strain has the D-lactate dehydrogenase according to claim 1 or a D-lactate dehydrogenase coded by the nucleotide sequence according to claim 2.

Further, in the above gene engineering strain, the L-lactate dehydrogenase gene is deactivated or deleted, and acetolactate synthase and/or acetolactate decarboxylase genes are deactivated or deleted.

Further, the above gene engineering strain further has one or more genes which are deactivated or deleted, and the one or more genes are selected from pyruvate formate-lyase gene, pyruvate formate-lyase activating enzyme gene, pyruvate dehydrogenase gene, acetokinase and ethanol dehydrogenase gene.

Further, an original strain of the above gene engineering strain is *Bacillus*. Further, the *Bacillus* are selected from a group consisting of *Bacillus licheniformis*, *Bacillus coagulans*, *B. subtilis*, *Bacillus amyloliquefaciens*, *Bacillus pumilus*, *Bacillus circulans* and *Aneurinibacillus aneurinilyticus*. Preferably, the original strain is *Bacillus licheniformis*. Preferably, the original strain is *Bacillus licheniformis* ATCC 14580. Preferably, the original strain is a ΔhsdR1ΔhsdR2 double-mutant strain MW3 of *Bacillus licheniformis* ATCC 14580.

Further, a promoter of the above D-lactate dehydrogenase gene is a promoter $P_{als}$ of α-acetolactate synthase of *Bacillus licheniformis* ATCC 14580, a $P_c$ promoter in plasmid pMMPc, a $P_{43}$ promoter in *B. subtilis* or a promoter $P_{ldh}$ of L-lactate dehydrogenase of *Bacillus licheniformis* ATCC 14580. Preferably, the promoter is directly connected with an original codon "ATG" of $ldh_{Ti}$ gene.

Further, the above gene engineering strain is *Bacillus licheniformis* BN11, the preservation number of which is CCTCC NO: M2016026 and which was preserved in China Center for Type Culture Collection on Jan. 8, 2016.

In still another aspect, the present invention provides a method for preparing the above gene engineering strain, comprising the following steps:

1) knocking out an L-lactate dehydrogenase gene in an original strain;

2) introducing the above nucleotide sequence coding the D-lactate dehydrogenase;

3) deactivating or deleting an acetolactate synthase gene and/or acetolactate decarboxylase gene; and 4) while or after performing step 3), adding a promoter sequence in the front of the nucleotide sequence introduced in step 2).

Specifically, by using a mutant strain MW3 of *Bacillus licheniformis* ATCC 14580 with the L-lactate dehydrogenase gene which is knocked out as a host, and replacing α-acetolactate decarboxylase (alsD) and acetolactate synthase (alsS) with the above D-lactate dehydrogenase, a heat-resistant engineering *Bacillus* strain CCTCC NO: M2016026 capable of producing D-lactic acid through fermentation at temperature of 30° C.-55° C. by using glucose is obtained.

In yet another aspect, the present invention further provides use of the above gene engineering strain, in particular use in production of D-lactic acid. Further, the strain is used for producing D-lactic acid by using glucose, xylose, maltose, lactose, sucrose or a combination thereof as a carbon source. Further, low-cost culture mediums containing peanut meal and dried corn steep liquor powder are used for fermentation. Further, D-lactic acid is produced through fermentation under an environment condition between an anaerobic environment condition and a microaerobic environment condition with pH of 6.0-8.0 and temperature of 45° C.-55° C. Further, the fermentation process is a continuous fermentation or fed-batch process.

Further, firstly seed culture is performed to the above gene engineering strain to obtain seed culture solution, and then fermentation culture is performed in fermentation culture mediums using one of glucose, xylose, maltose, lactose and sucrose as a carbon source and using yeast powder, peptone, peanut meal and dried corn steep liquor as a nitrogen source to obtain D-lactic acid. Specifically, the process comprises the following steps:

1) slant culture: inoculating an engineered *Bacillus* strain into a solid slant culture medium containing 20 g/L agar and culturing for 24-48 h at 45-55° C.;

2) seed culture: inoculating the engineered *Bacillus* after slant culture into a seed culture medium under an aseptic condition, statically culturing for 24-36 h at 45-55° C. to obtain seed culture solution, wherein a neutralizing agent is added to control pH of fermentation liquid; and 3) fermentation culture: inoculating the seed culture solution into a fermentation culture medium in an inoculation amount according to a volume ratio of 5-20%, and culturing for 48-90 h at 45° C.-55° C., wherein the temperature is preferably 50° C.

Preferably, each liter of the seed culture medium in step 2) contains 60-120 g of glucose or 40-70 g of xylose, 8-12 g of yeast powder, 3-8 g of peptone, 50 g of calcium carbonate and balance of water, and preferably contains 90 g of glucose, 10 g of yeast powder, 5 g of peptone, 50 g of calcium carbonate and balance of water; and pH of the seed culture medium is 6.0. Sterilization is performed for 15 min at 115° C. The neutralizing agent comprises one or more of NaOH, NH$_4$OH and Ca(OH)$_2$.

Preferably, the fermentation culture medium in step 3) comprises the following components and contents thereof: 40-180 g/L carbon source and 5-20 g/L nitrogen source. Preferably, the fermentation process in step 3) is a fed-batch process, and the fed-batch process refers to that, when the total content of reducing sugars in the fermentation liquid is lower than 20 g/L, the carbon source is added to enable the total content of the reducing sugars to be maintained at 30-70 g/L or reach 50-70 g/L. Preferably, pH of the fermentation culture medium is 6.0-8.0.

The reconstructed gene engineering strain provided by the present invention can produce, by fermentation, high-concentration and highly optically-pure D-lactic acid at higher fermentation temperature by using low-cost raw materials, which can improve the production efficiency while the cost is reduced, so that the production cost is reduced and the method is suitable for application and dissemination in industrial production. The highest yield of D-lactic acid can reach 226 g/L with an optical purity of 99.9%, the highest sugar-acid conversion rate can reach 93.6% and the fermentation production capacity is 3.2 g/[L·h]. Therefore, by using the inventive method to produce D-lactic acid, the cost can be reduced, the operation flow can be simplified and the method has a wide industrial application prospect.

The concept, specific steps and produced technical effects of the present invention will be further described below with reference to the drawings, so as to fully understand the purposes, features and effects of the present invention.

BRIEF DESCRIPTION OF THE DRAWINGS

FIG. 13 shows analysis results of enzyme catalytic sites obtained through amino acid sequence comparison between an amino acid sequence (query) expressed by SEQ ID No. 1 and other D-lactate dehydrogenases (SEQ ID Nos: 85-93).

FIG. 14 shows analysis results of ligand binding sites obtained through amino acid sequence comparison between an amino acid sequence (query) expressed by SEQ ID No. 1 and other D-lactate dehydrogenases (SEQ ID Nos: 85-93).

FIG. 15 shows analysis results of NAD binding sites obtained through amino acid sequence comparison between an amino acid sequence (query) expressed by SEQ ID No. 1 and other D-lactate dehydrogenases (SEQ ID Nos: 85-93).

DETAILED DESCRIPTION OF THE PREFERRED EMBODIMENTS

In one aspect, the present invention provides a D-lactate dehydrogenase, which is capable of catalyzing pyruvic acid to synthesize D-lactic acid.

In one preferred specific implementation mode, the D-lactate dehydrogenase has one of the following amino acid sequences:

1) an amino acid sequence expressed by SEQ ID No. 1;

2) an amino acid sequence derivatively produced from the amino acid sequence expressed by SEQ ID No. 1 through substitution, deletion, insertion or addition of one or more amino acid residues;

3) an amino acid sequence produced from the amino acid sequence expressed by SEQ ID No. 1 through conservative replacement; and 4) an amino acid sequence having at least 80% of homology with the amino acid sequence expressed by SEQ ID No. 1.

"Conservative replacement" described here should be understood as those substitutions in which given amino acids in a polypeptide are substituted with another type of amino acids with similar features. Typically, the following replacement is considered as conservative substitution: replacing aliphatic amino acids such as Ala, Val, Leu and Ile with another aliphatic amino acids; replacing Ser with Thr, vice versa; replacing acidic residues of Asp or Glu with another acidic residues; replacing acylamino-containing residues of Asn or Gln with another acylamino-containing residues; replacing alkaline residues of Lys or Arg with another alkaline residues; and replacing aromatic residues of Phe or Tyr with another aromatic residues.

Functionally equivalent amino acids generally are similar to amino acids replaced thereby in aspects of size and/or feature (such as charge or hydrophobicity) Amino acids with similar features can be grouped as follows:

(1) hydrophobic amino acids: His, Trp, Trp, Tyr, Phe, Met, Leu, Ile, Val, and Ala;
(2) neutrally hydrophobic amino acids: Cys, Ser, and Thr;
(3) polar amino acids: Ser, Thr, Asn, and Gln;
(4) acidic/negatively charged amino acids: Asn, Lys, and His;
(5) charged amino acids: Asp, Glu, Asn, Lys, and His;
(6) alkaline/positively charged amino acids: Asn, Lys, and His;
(7) alkaline amino acids: Asn, Gln, His, Lys, and Arg;
(8) amino acids with residues influencing chain orientations: Gly, Pro; and
(9) aromatic amino acids: Trp, Tyr, Phe, and His.

Figure 12:
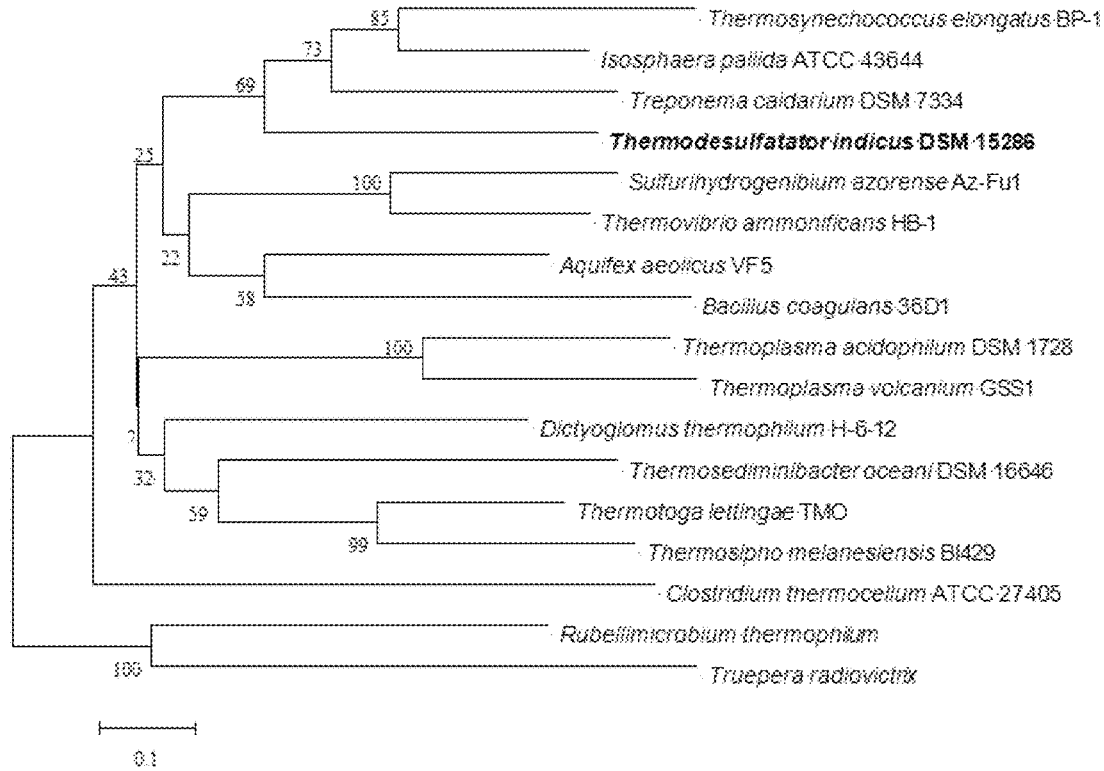
FIG. 12 is a phylogenetic tree of D-lactate dehydrogenases predicted in partial typical *Thermophilus*.

A phylogenetic tree, drawn by using MEGA 5 software and a neighbor-joining method, of amino acid sequences of D-lactate dehydrogenases predicted in partial typical *Thermophilus* is as illustrated in FIG. 12, wherein a strain expressed with a bold font is a donor strain of the D-lactate dehydrogenase expressed by SEQ ID No. 1, the D-lactate dehydrogenase having the lowest homology with the D-lactate dehydrogenase expressed by SEQ ID No. 1 is a D-lactate dehydrogenase in *Truepera radiovictrix*, and the similarity between the two amino acids for the two D-lactate dehydrogenases is 28%; and the D-lactate dehydrogenase having the highest homology with the D-lactate dehydrogenase expressed by SEQ ID No. 1 is a D-lactate dehydrogenase in *Treponema caldarium* DSM 7334, and the similarity between the two amino acids for the two D-lactate dehydrogenase is 45%.

Figure 13:
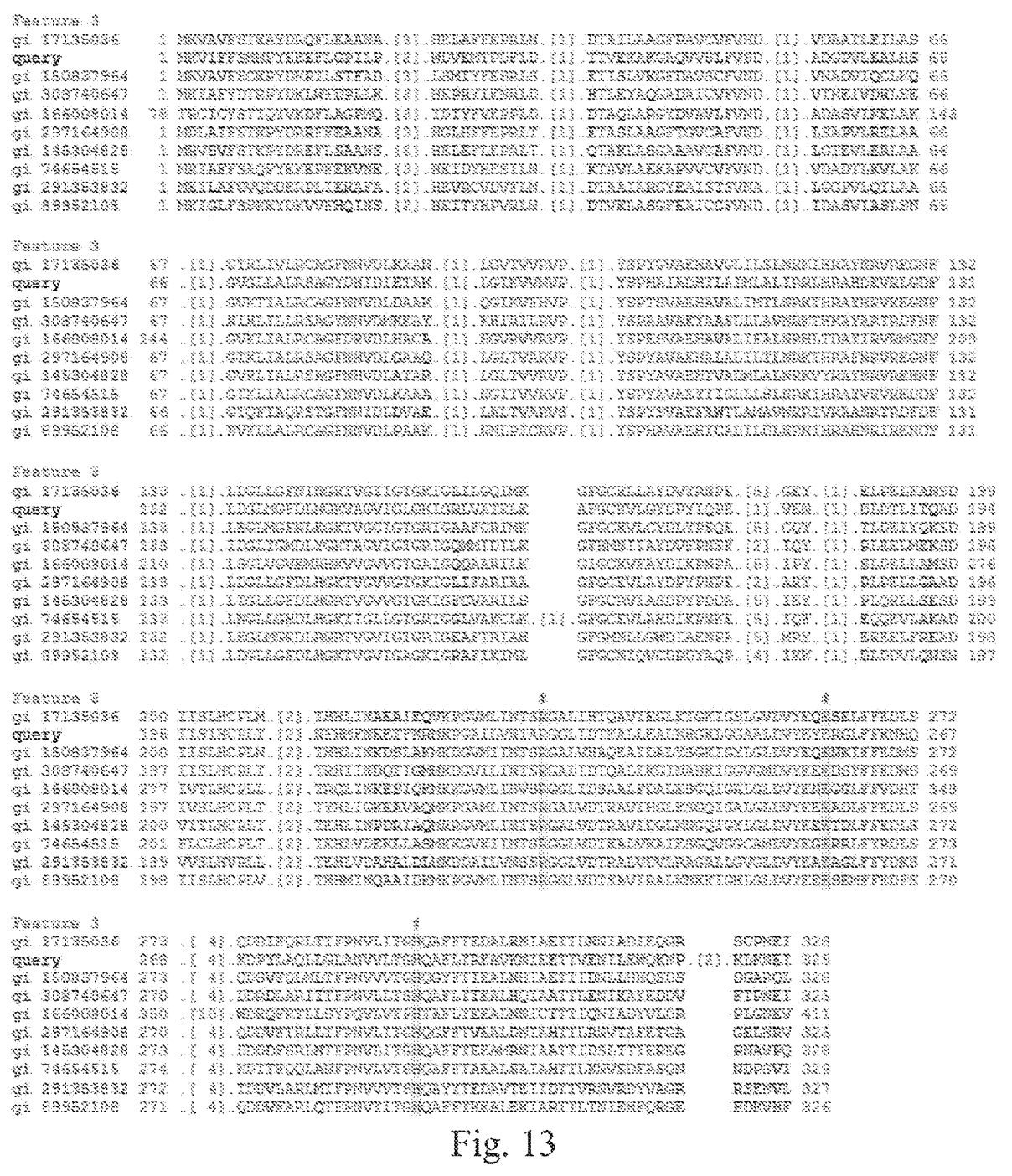
Figure 14:
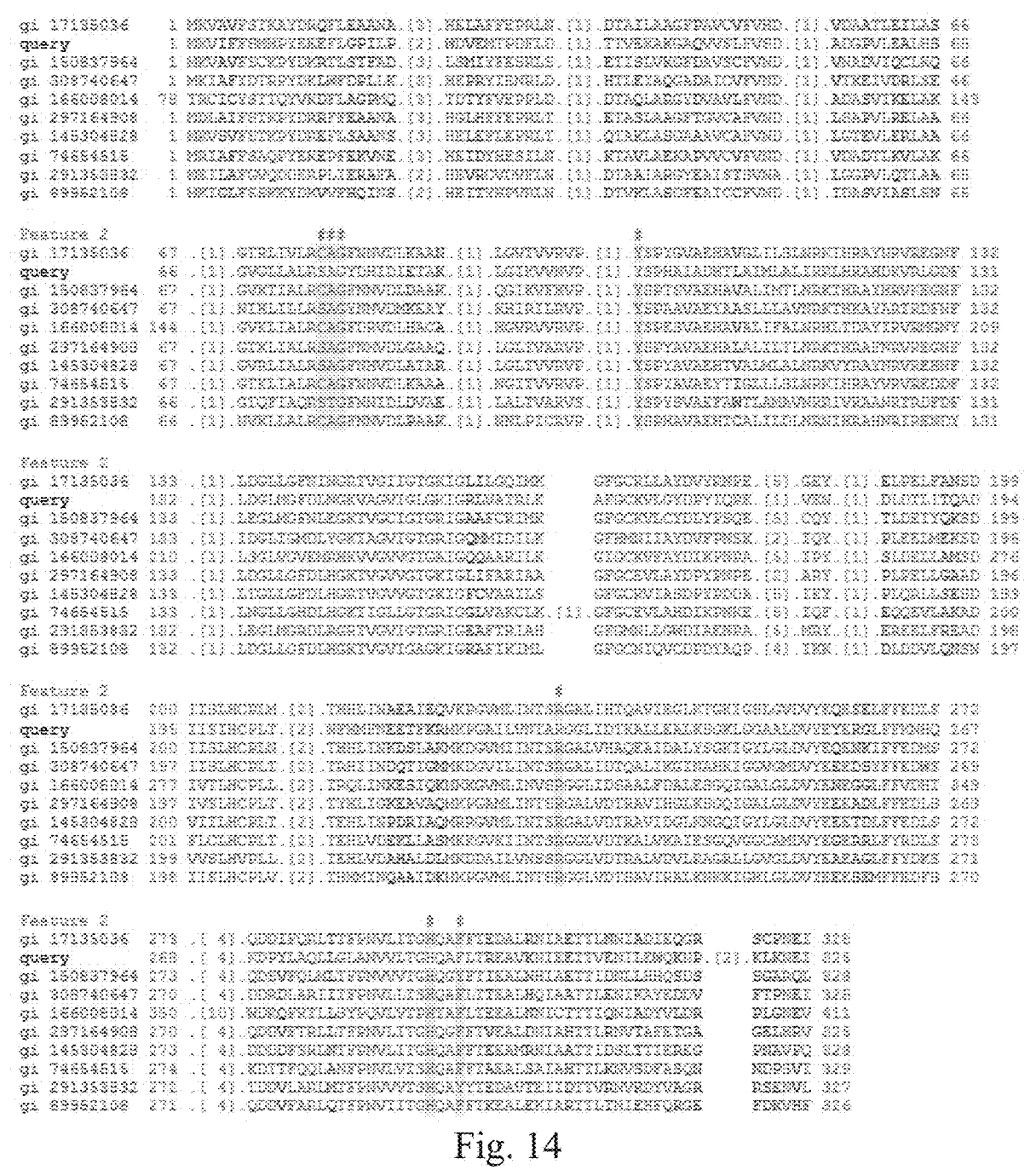
Figure 15:
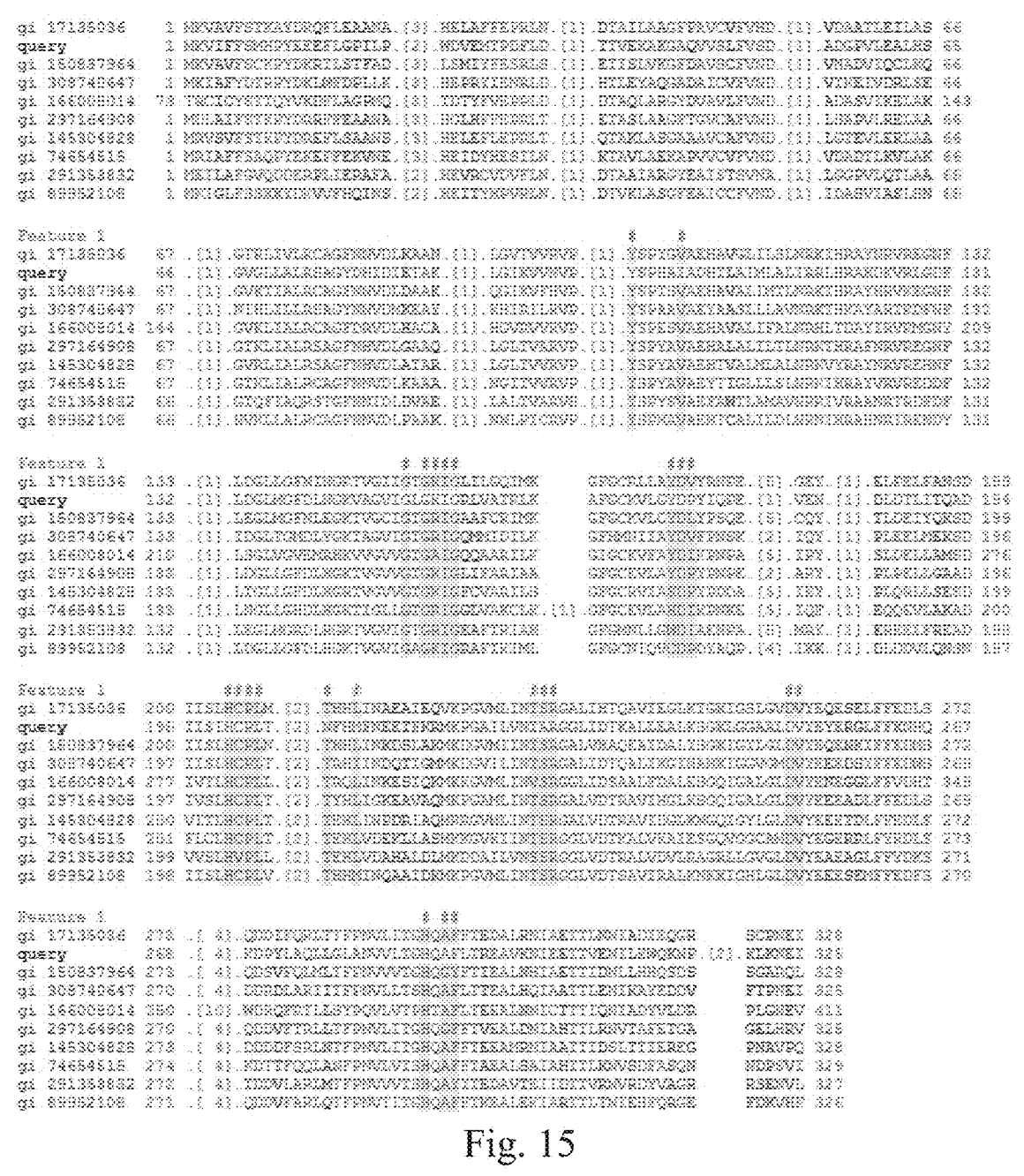

Preferably, the substitution, deletion, insertion or addition of the amino acid residues occurs outside a functional domain comprising enzyme catalytic sites, ligand binding sites and NAD binding sites of the D-lactate dehydrogenase Amino acid sequence comparison is performed between the amino acid sequence expressed by SEQ ID No. 1 and other D-lactate dehydrogenases, so as to obtain comparison analysis results for catalytic sites, ligand binding sites and NAD binding sites as illustrated in FIG. 13, FIG. 14 and FIG. 15.

More preferably, the substitution, deletion, insertion or addition of the amino acid residues occurs outside key amino acids at enzyme catalytic sites, ligand binding sites and NAD binding sites. Herein, key amino acids at the enzyme catalytic sites are Arg at position 229, Glu at position 258 and His at position 290; key amino acids at the ligand binding sites are Ser, Ala and Gly positions 75-77, Tyr at position 99, Arg at position 229, His at position 290 and Phe at position 293; and key amino acids at the NAD binding sites are Tyr at position 99, Ile at position 104, Gly at position 150, Gly, Lys, Ile and Gly at positions 152-155, Tyr, Asp and Pro at positions 172-174, His, Cys, Pro and Leu at positions 199-202, Asn at position 206, Met at position 209, Thr, Ala and Arg at positions 227-229, Asp and Val at positions 253 and 254, His at position 290, and Ala and Phe at positions 292 and 293.

In another aspect, the present invention provides a nucleotide sequence coding the above D-lactate dehydrogenase.

In one preferred specific implementation mode, the nucleotide sequence is one of the following nucleotide sequences:

1) a nucleotide sequence expressed by SEQ ID No. 2;
2) a nucleotide sequence expressed by SEQ ID No. 3;
3) a nucleotide sequence having more than 80% of homology with the nucleotide sequence expressed by SEQ ID No. 2 or SEQ ID No. 3; and
4) a nucleotide sequence hybridized with a complementary chain of the nucleotide sequence expressed by SEQ ID No. 2 or SEQ ID No. 3 under a high-stringency condition.

"Hybridization under low-stringency, medium-stringency, high-stringency or extremely-high-stringency condition" described herein describes conditions for hybridization and washing. Guidance for performing a hybridization reaction can be seen in Current Protocols in Molecular Biology, John Wiley & Sons, N.Y. (1989), 6.3.1-6.3.6. In this literature, a liquid-phase hybridization method and a non-liquid-phase hybridization method are described and either of them is usable. Specific hybridization conditions herein are as follows: 1) a low-stringency hybridization condition refers to hybridization at about 45° C. in 6× sodium chloride/sodium citrate (SSC), and then washing twice at 50° C. at least (for low-stringency conditions, washing temperature shall be increased to 55° C.) in 0.2×SSC, and 0.1% SDS; 2) a medium-stringency hybridization condition refers to hybridization at about 45° C. in 6×SSC, and then washing one or more times at 60° C. at least in 0.2×SSC, and 0.1% SDS; 3) a high-stringency hybridization condition refers to hybridization at about 45° C. in 6×SSC, and then washing one or more times at 65° C. in 0.2×SSC, and 0.1% SDS; and 4) an extremely-high-stringency hybridization condition refers to hybridization at 65° C. in 0.5M sodium phosphate, and 7% SDS, and then washing one or more times at 65° C. at least in 0.2×SSC, and 0.1% SDS. The high-stringency condition (3) is preferred and should be used unless otherwise specially pointed out.

In another aspect, the present invention provides a gene engineering strain, which has the D-lactate dehydrogenase as described above or a D-lactate dehydrogenase coded by the nucleotide sequence as described above.

In one specific implementation mode, in the original strain of the gene engineering strain, a pathway for synthesizing L-lactic acid by pyruvic acid and a pathway for synthesizing 2,3-butanediol by pyruvic acid are blocked. In one embodiment, the pathway for synthesizing L-lactic acid by pyruvic acid is blocked by deactivating or deleting an L-lactate dehydrogenase gene; and the pathway for synthesizing 2,3-butanediol by pyruvic acid is blocked by deactivating or deleting one or both of an acetolactate synthase gene and an acetolactate decarboxylase gene.

In another specific implementation mode, in addition to the blocked pathways as mentioned above, one or more of a pathway for synthesizing formic acid by pyruvic acid, a pathway for synthesizing acetic acid by pyruvic acid and a pathway for synthesizing ethanol by pyruvic acid are blocked in the original strain. The pathway for synthesizing formic acid by pyruvic acid is blocked by deactivating or deleting one or both of a pyruvate formate-lyase gene and a pyruvate formate-lyase activating enzyme gene; the pathway for synthesizing acetic acid by pyruvic acid is blocked by deactivating or deleting one or both of a pyruvate dehydrogenase gene and an acetokinase gene; and the pathway for synthesizing ethanol by pyruvic acid is blocked by deactivating or deleting one or both of a pyruvate dehydrogenase gene and an ethanol dehydrogenase gene.

Preferably, an original strain is *Thermophilus*. More preferably, a restrictive modification system in the original strain is deactivated or knocked out.

Preferably, a promoter of a gene of the above D-lactate dehydrogenase is reconstructed into a constitutive promoter, i.e., no inducer is needed; and the regulation of the constitutive promoter is not influenced by external conditions and the expression of the promoter gene has continuity.

Figure 1:
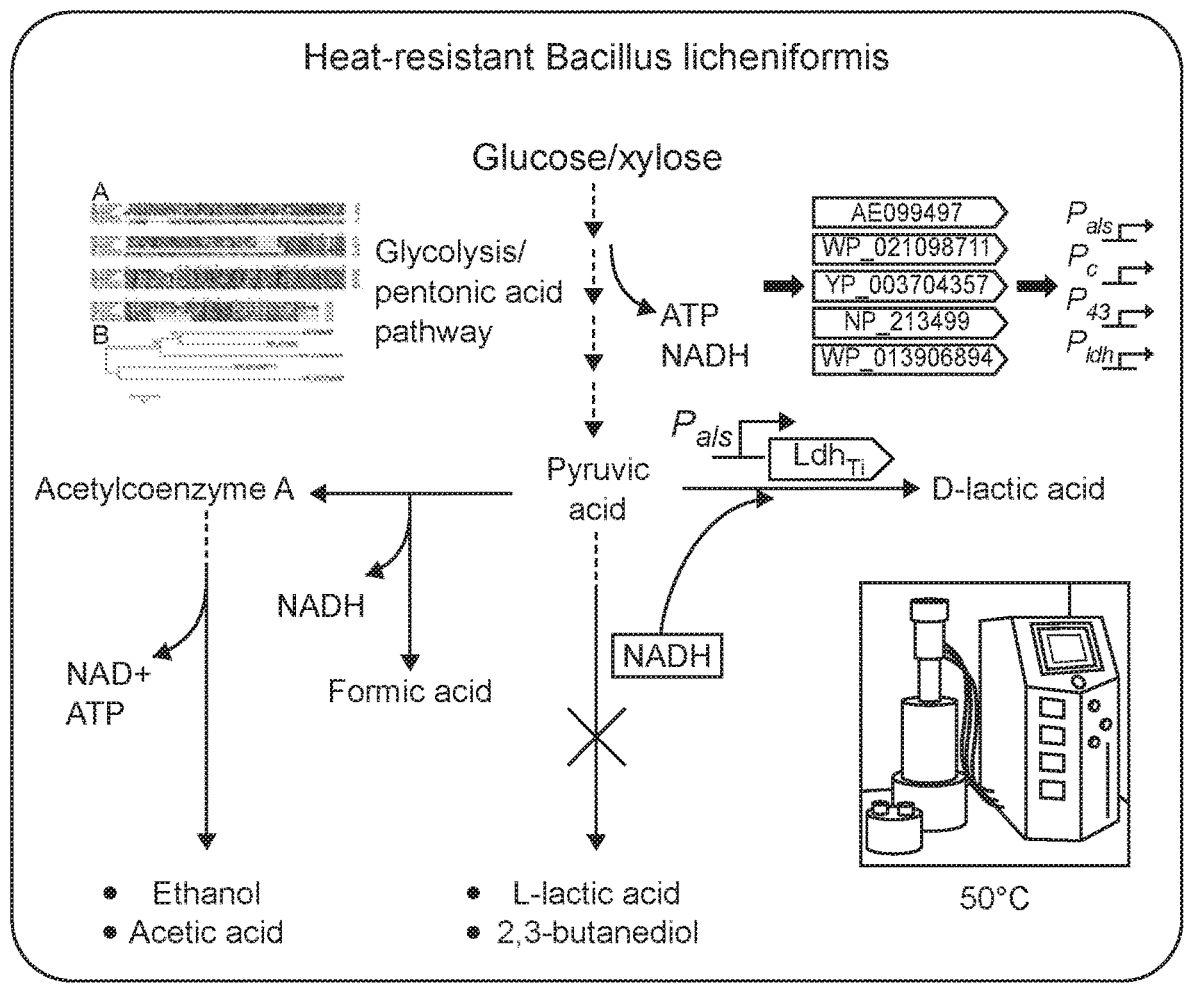
FIG. 1 is a schematic diagram of construction of heat-resistant *Bacillus licheniformis* and a pathway to produce D-lactic acid according to one specific implementation mode of the present invention.

FIG. 1 is a schematic diagram of construction of D-lactic acid engineered strain and a pathway to produce D-lactic acid according to one embodiment.

"Block" herein refers to blocking a certain pathway through various gene engineering methods, including deactivating or deleting genes for one or more catalytic enzymes in this pathway such that this pathway is unworkable.

"Original D-lactate dehydrogenase gene" herein refers to a D-lactate dehydrogenase gene carried by the original strain itself.

One skilled in the art can understand that the original strain may also not contain the deleted or deactivated enzyme gene or the blocked pathways, such as L-lactate dehydrogenase gene and D-lactate dehydrogenase gene or the like. Thus, when the gene engineering strain is constructed, these genes or pathways are naturally deleted, and are not required to be deactivated, deleted or blocked by performing additional gene engineering operations.

In another aspect, the present invention provides use of the above gene engineering strain, in particular use in production of D-lactic acid.

In one specific implementation mode, the gene engineering strain may produce D-lactic acid through fermentation by using a carbon source which is one or more selected from a group consisting of glucose, xylose, maltose, lactose and sucrose; and may also produce D-lactic acid through fermentation by using low-cost culture mediums containing peanut meal and dried corn steep liquor powder. Since the original strain for the gene engineering strain is *Thermophilus* and the original source of the introduced D-lactate dehydrogenase is also *Thermophilus*, the gene engineering strain can produce D-lactic acid at higher fermentation temperature.

The present invention will be further described in detail below in combination with the embodiments.

Unless otherwise specially stated, experimental methods used in the following embodiments are all conventional methods. Unless otherwise specially stated, materials, reagents, strains and the like used in the following embodiments can be commercially available.

Reagents and strains: all reagents in the present invention were reagents which were commercially available and reagent grade or higher. Herein, FastPfu DNA polymerases were available from Beijing TransGen Biotech Co., Ltd. All restriction endonucleases and $T_4$ DNA ligases were available from NEB (New England Biolabs). Isopropyl-beta-D-thiogalactopyranoside (IPTG), dithiothreitol (DTT) and phenylmethylsulfonyl fluoride (PMSF) were available from Merck KGaA. L-lactic acid and D-lactic acid standard products were available from Sigma-Aldrich Corporation. pMD18-T and all primers were synthesized in TaKaRa (Dalian). *Bacillus licheniformis* ATCC 14580 may be directly available from ATCC website, double-mutant strains MW3 (ΔhsdR1, ΔhsdR2) of *Bacillus licheniformis* ATCC 14580 may be constructed according to the method in literature Generation of Readily Transformable *Bacillus licheniformis* Mutants (Bianca Was chkaw et al., Appl Microbiol Biotechnol, (2008) 78:181-188), and the double-mutant strains MW3 were used as host bacteria during DNA operations. *E. coli* DH5α and BL21 (DE3) were used as cloning host and expression host bacterium, respectively. *E. coli* S17-1 were used as donor bacteria for conjugal transfer. pETDuet-1 was used as an expression vector. Shuttle plasmid pKVM1 was resistant to penbritin and erythrocin and used for knocking out genes of *Bacillus licheniformis* MW3. Luria-Bertani (LB) culture mediums were used for culturing *E. coli* and *Bacillus*. Penbritin (100 g/mL), erythrocin (5 g/mL) and polymyxin B (40 g/mL) were used for screening *E. coli* and *Bacillus*. X-Gal (40 g/mL) was used for blue-white screening.

HPLC analysis for D-lactic acid produced by strains was performed by using a chiral column MCI GEL CRS10W.

Embodiment 1: Obtaining of D-Lactate Dehydrogenase Gene and Protein Thereof

1. Obtaining of D-lactate Dehydrogenase $Ldh_{Ti}$ Gene

By using D-lactate dehydrogenase NP_213499 in *Aquifex aeolicus* VF5 as a template in NCBI, a protein WP_013906894 which had a similarity of 38% with NP_213499 and was possibly D-lactate dehydrogenase was obtained through comparison, and a sequence thereof was as expressed by SEQ ID No. 1. Through further search, it was found that this protein existed in *Thermodesulfatator indicus* DSM 15286, a corresponding nucleotide sequence thereof was a complete open reading frame, as expressed by SEQ ID No. 2, with a length of 978 bp, coding a protein consisting of amino acid residues expressed by SEQ ID No. 1, and the protein was named as $Ldh_{Ti}$. After optimization according to the codon of *E. coli* K12, a synthesis process was performed by a PCR synthesis method, and by adopting primers shown in Table 1 in which the primers served as templates for each other, thereby synthesizing a nucleotide sequence optimized by the codon with a sequence thereof as expressed by SEQ ID No. 3. The obtained gene as expressed by SEQ ID No. 3 was inserted into a pMD18-T vector to obtain a pMD18-T-$ldh_{Ti}$ plasmid, and nucleotide sequence determination was performed. One skilled in the art can understand that the gene expressed by SEQ ID No. 3 may also be directly synthesized by means of gene synthesis.

TABLE 1

Sequences of primers for synthesis of D-lactate dehydrogenase $Ldh_{Ti}$, through PCR

| Primer | Sequence (5'-3') |
|---|---|
| P1 | CCGC<u>GGATCC</u>GATGAAAGTAATTTTTTT (SEQ ID No. 4) |
| P2 | TCTTCATACGGGTGCATAGAAAAAAAAATTACTTTCATCGGA TCCG (SEQ ID No. 5) |
| P3 | TTCTATGCACCCGTATGAAGAGGAATTTCTGGGTCCGATTCT GCC (SEQ ID No. 6) |
| P4 | GGGGTCATTTCTACGTCCCAGTCAGACGGCAGAATCGGACCC AGA (SEQ ID No. 7) |
| P5 | GGGACGTAGAAATGACCCCGGACTTTCTGGACGAAACCACCG TGG (SEQ ID No. 8) |
| P6 | CTTACTACCTGGGCACCTTTAGCCTTTTCCACGGTGGTTTCG TCC (SEQ ID No. 9) |
| P7 | TAAAGGTGCCCAGGTAGTAAGCCTGTTTGTTTCTGACAAAGC TGA (SEQ ID No. 10) |
| P8 | GCAGCGCTTCCAGTACCGGACCATCAGCTTTGTCAGAAACAA ACA (SEQ ID No. 11) |
| P9 | GGTACTGGAAGCGCTGCATTCTTACGGTGTGGGCCTGCTGGC CCT (SEQ ID No. 12) |
| P10 | AATATCGATGTGATCATAGCCAGCAGAACGCAGGGCCAGCAG GCC (SEQ ID No. 13) |

TABLE 1-continued

Sequences of primers for synthesis of D-lactate dehydrogenase Ldh$_{Ti}$, through PCR

| Primer | Sequence (5'-3') |
|---|---|
| P11 | CTGGCTATGATCACATCGATATTGAGACCGCAAAACGCCTGGGTA (SEQ ID No. 14) |
| P12 | GAATAGGCTGGCACGTTAACTACTTTGATACCCAGGCGTTTTGCG (SEQ ID No. 15) |
| P13 | AGTTAACGTGCCAGCCTATTCTCCGCACGCTATCGCTGACCATAC (SEQ ID No. 16) |
| P14 | AATCAGAGCCAGCATGATAGCCAGAGTATGGTCAGCGATAGCGTG (SEQ ID No. 17) |
| P15 | GCTATCATGCTGGCTCTGATTCGTCGTCTGCACCGTGCCCATGAT (SEQ ID No. 18) |
| P16 | CCAGATCAAAATCACCCAGGCGCACTTTATCATGGGCACGGTGCA (SEQ ID No. 19) |
| P17 | CCTGGGTGATTTTGATCTGGATGGTCTGATGGGCTTTGATCTGAA (SEQ ID No. 20) |
| P18 | CCAATTACACCAGCAACTTTGCCGTTCAGATCAAAGCCCATCAGA (SEQ ID No. 21) |
| P19 | GCAAAGTTGCTGGTGTAATTGGTCTGGGTAAAATCGGTCGCCTGG (SEQ ID No. 22) |
| P20 | ACCAAACGCTTTCAGGCGGGTAGCTACCAGGCGACCGATTTTACC (SEQ ID No. 23) |
| P21 | CGCCTGAAAGCGTTTGGTTGCAAAGTTCTGGGCTATGATCCATAC (SEQ ID No. 24) |
| P22 | TTTTCTACGATTTCCGGCTGAATGTATGGATCATAGCCCAGAACT (SEQ ID No. 25) |
| P23 | TCAGCCGGAAATCGTAGAAAACGTTGATCTGGATACCCTGATCAC (SEQ ID No. 26) |
| P24 | ATGAATAGAAATGATATCAGCCTGAGTGATCAGGGTATCCAGATCAA (SEQ ID No. 27) |
| P25 | TCAGGCTGATATCATTTCTATTCATTGTCCGCTGACCCGTGAAAA (SEQ ID No. 28) |
| P26 | AAAGTCTCTTCGTTAAACATATGAAAGTTTTCACGGGTCAGCGGA (SEQ ID No. 29) |
| P27 | CTTTCATATGTTTAACGAAGAGACTTTTAAGCGTATGAAACCGGGTG (SEQ ID No. 30) |
| P28 | CCACGCGCGGTGTTAACCAGAATAGCACCCGGTTTCATACGCTTA (SEQ ID No. 31) |
| P29 | GTTAACACCGCGCGTGGTGGTCTGATCGATACCAAGGCCCTGCTG (SEQ ID No. 32) |
| P30 | GCCCAGTTTACCAGACTTCAGGGCCTCCAGCAGGGCCTTGGTATC (SEQ ID No. 33) |
| P31 | CTGAAGTCTGGTAAACTGGGCGGCGCAGCCCTGGATGTGTATGAA (SEQ ID No. 34) |
| P32 | TTTTAAAAAACAGGCCACGTTCATATTCATACACATCCAGGGCTG (SEQ ID No. 35) |
| P33 | GAACGTGGCCTGTTTTTAAAAACCACCAAAAAGAAGGTATCAAA (SEQ ID No. 36) |
| P34 | GCAGCTGGGCCAGATACGGGTCTTTGATACCTTCTTTTTGGTGGT (SEQ ID No. 37) |
| P35 | CGTATCTGGCCCAGCTGCTGGGTCTGGCCAACGTAGTGCTGACCG (SEQ ID No. 38) |

TABLE 1-continued

Sequences of primers for synthesis of D-lactate dehydrogenase Ldh$_{Ti}$, through PCR

| Primer | Sequence (5'-3') |
|---|---|
| P36 | CCTCACGGGTCAGAAAGGCCTGATGACCGGTCAGCACTACGTTGG (SEQ ID No. 39) |
| P37 | CCTTTCTGACCCGTGAGGCTGTAAAAAACATCGAAGAAACTACCG (SEQ ID No. 40) |
| P38 | TTGCCATTCCAGAATGTTTTCTACGGTAGTTTCTTCGATGTTTTTTAC (SEQ ID No. 41) |
| P39 | TAGAAAACATTCTGGAATGGCAAAAGAACCCGCAGGCAAAGCTGA (SEQ ID No. 42) |
| P40 | GCCC<u>AAGCTT</u>TTAGATTTCGTTTTTCAGCTTTGCCTGCGG (SEQ ID No. 43) |

Underlines represents enzyme cutting sites.

2. Construction of Recombinant Prokaryotic Expression Vector

PCR amplification was performed to the obtained pMD18-T-ldhTi plasmid by using primers 1 and 40 as shown in Table 1, the obtained target gene segments were digested with two enzymes BamHI and HindIII, then the segments were linked to an expression vector pETDuet-1 (Novagen) which was also subjected to a double enzyme digestion treatment using the same enzymes, a linked product containing the Ldh$_{Ti}$ gene was transformed into E. coli BL21 (DE3) (Novagen), and after a PCR process and an identification process by DNA sequencing, a plasmid in a positive clone containing correct Ldh$_{Ti}$ gene was named as pETDuet-ldh$_{Ti}$, and it can be used for expression of the D-lactate dehydrogenase.

3. Prokaryotic Expression and Purification of D-Lactate Dehydrogenase

1) Prokaryotic Expression of D-Lactate Dehydrogenase Ldh$_{Ti}$

The obtained E. coli BL21 (DE3) containing the prokaryotic expression vector pETDuet-ldh$_{Ti}$ was shaken at 37° C. till OD$_{600\ nm}$ was 0.6-0.8, and then was added with IPTG with a final concentration of 1 mM for induction, the obtained mixture was in a shaker for culture for 16 h at 16° C. or for 8 h at 30° C., then the cultured bacteria cells were collected by centrifugation, resuspended in 50 mM phosphate buffer solution (PBS; pH 7.4), and broken by an ultrasonic wave manner, and then the supernatant was collected for SDS-PAGE electrophoretic analysis.

Figure 2:
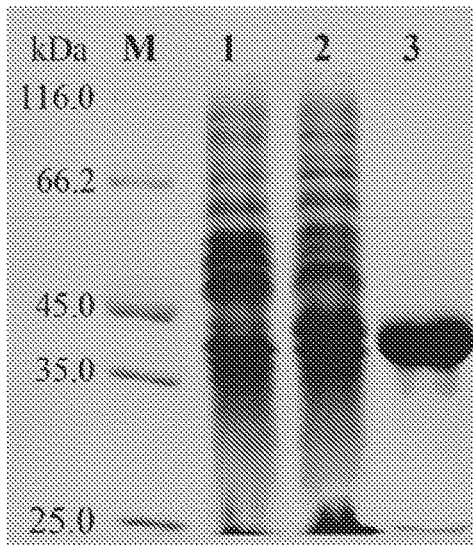
FIG. 2 is molecular weight of purified D-lactate dehydrogenase protein detected through SDS-PAGE, wherein lane M is a protein molecular weight standard; lane 1 shows crude enzyme liquid obtained after inducing *E. coli* BL21 (DE3) containing pETDuet-1 empty vectors; lane 2 shows crude enzyme liquid obtained after inducing *E. coli* BL21 (DE3) containing prokaryotic expression vectors pETDuet-ldh$_B$; and lane 3 shows purified D-lactate dehydrogenase.

Results are as shown in FIG. 2, from which it can be seen that the prokaryotic expression vectors pETDuet-ldh$_{Ti}$ carrying the target gene are abundantly expressed in E. coli BL21 (DE3), and the single subunit molecular weight of the expressed recombinant protein is about 37 kDa, which is compliant with the expected result.

2) Purification of D-Lactate Dehydrogenase Ldh$_{Ti}$

The proteins expressed in step 1) were purified through His-tag, which was specifically as follows:

The prokaryotic expression product obtained in step 1), which was detected by SDS-PAGE, was purified by affinity chromatography, i.e., the supernatant after ultrasonication was passed through a chromatographic column filled with Ni-NTA gel, the proteins containing His-tag were bound to the Ni-NTA gel, then non-specifically bound impure proteins were washed away by cleaning buffer solution (25 mM Tris hydrochloric acid buffer solution, 500 mM NaCl, and 50 mM imidazole, wherein the above-mentioned concentrations were final concentrations in solution, PH 8.0), and the target proteins were finally eluted by elution buffer solution (25 mM Tris hydrochloric acid buffer solution, 500 mM NaCl, and 220 mM imidazole, wherein the above-mentioned concentrations were final concentrations in solution, PH 8.0) to obtain the purified target proteins. Then, by using a molecular sieve gel column and replacing the buffer solution with 50 mM phosphate buffer solution (pH 7.0), the final purified target proteins D-lactate dehydrogenase $Ldh_{Ti}$ was obtained.

SDS-PAGE electrophoresis was performed to the final purified target proteins D-lactate dehydrogenase $Ldh_{Ti}$, and a result is as shown in lane 3 of FIG. 2, wherein the target band is single, and the size is about 37 kDa, indicating that the obtained target proteins are relatively pure.

Embodiment 2: Enzymatic Characteristic Identification of Target Protein D-Lactate Dehydrogenases $Ldh_{Ti}$ Obtained in Embodiment 1

The enzymatic characteristic of the target protein obtained in Embodiment 1 was identified by using the following substrates: pyruvic acid, D-lactic acid, L-lactic acid, glyceric acid, phenylpyruvic acid, glyoxylic acid and oxaloacetic acid. A reaction system is consisting of: 50 mM phosphate buffer solution (pH 7.0), 0.2 mM NADH or NAD$^+$ as coenzyme, a suitable amount of D-lactate dehydrogenases $Ldh_{Ti}$ and substrates with different concentrations, reacted at 37° C. An enzyme activity determination method is to determine oxidization of NADH or reduction of NAD$^+$ at ultraviolet wavelength of 340 nm, wherein one enzyme activity unit is defined as the enzyme amount needed for oxidizing or reducing 1 μmoL NADH or NAD$^+$ in one minute.

Results show that the target proteins obtained in Embodiment 1 can catalyze pyruvic acid, glyoxylic acid, oxaloacetic acid, D-lactic acid and phenylpyruvic acid, but have no activity for L-lactic acid and glyceric acid (Table 2). Particularly, D-lactate dehydrogenases $Ldh_{Ti}$ have the highest catalytic efficiency for pyruvic acid and can specifically catalyze D-lactic acid. Therefore, the above-mentioned results show that the target proteins obtained in Embodiment 1 are D-lactate dehydrogenases $Ldh_{Ti}$ indeed.

TABLE 2

Ranges for Substrate Spectrums Catalyzed by D-lactate Dehydrogenases $Ldh_{Ti}$

| Substrate | $K_m$ mM | $k_{cat}$ min$^{-1}$ | $k_{cat}/K_m$ M$^{-1}$ min$^{-1}$ |
|---|---|---|---|
| Pyruvic Acid | 0.05 ± 0.01 | 64.7 ± 1.70 | (1.24 ± 0.04) × 10$^6$ |
| L-lactic Acid | — | — | — |
| D-lactic Acid | 5.41 ± 0.28 | 6.29 ± 0.30 | (1.16 ± 0.03) × 10$^3$ |
| Glyoxylic Acid | 1.76 ± 0.08 | 137.8 ± 3.10 | (7.83 ± 0.29) × 10$^4$ |
| Oxaloacetic Acid | 1.32 ± 0.05 | 268.4 ± 5.90 | (2.03 ± 0.07) × 10$^5$ |
| Phenylpyruvic Acid | 4.58 ± 0.24 | 17.7 ± 0.68 | (3.86 ± 0.22) × 10$^3$ |
| Glyceric Acid | — | — | — |

"—" represents that the enzyme has no activity for the substrate.

Figure 3:
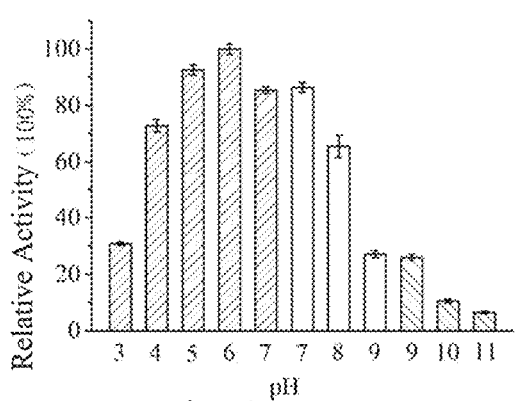
FIG. 3 is a determination result of the optimal reaction pH value s of D-lactate dehydrogenase.

Herein, the optimal reaction pH value and the optimal reaction temperature for the D-lactate dehydrogenases $Ldh_{Ti}$ obtained in Embodiment 1 were determined through the following two tests:

1) Determination of the Optimal Reaction pH Value of D-Lactate Dehydrogenases $Ldh_{Ti}$ An enzyme activity determination method is to determine change in NADH at ultraviolet wavelength of 340 nm, and one enzyme activity unit is defined as the enzyme amount needed for oxidizing 1 μmoL of NADH in one minute. At 37° C., by using 20 mM pyruvic acid as a substrate and 0.2 mM NADH as a coenzyme, the change of enzyme activity of the D-lactate dehydrogenase within a pH range of 3.0-11.0 was determined. A buffer system is consisting of: 50 mM citric acid-sodium citrate buffer solution with pH of 3.0-7.0; 50 mM phosphate buffer solution with pH of 7.0-9.0; and 50 mM sodium carbonate-sodium hydrogen carbonate buffer solution with pH of 9.0-11.0. Experiments were repeated thrice. A result is as shown in FIG. 3, wherein the optimal reaction pH value of this enzyme is 6.0. Relative enzyme activities in FIG. 3 are relative enzyme activities, which are obtained by: determining enzyme activities at different pH values, and correspondingly converting the enzyme activity values at other pH values on the basis that the highest value at pH 6.0 is 100%.

Figure 4:
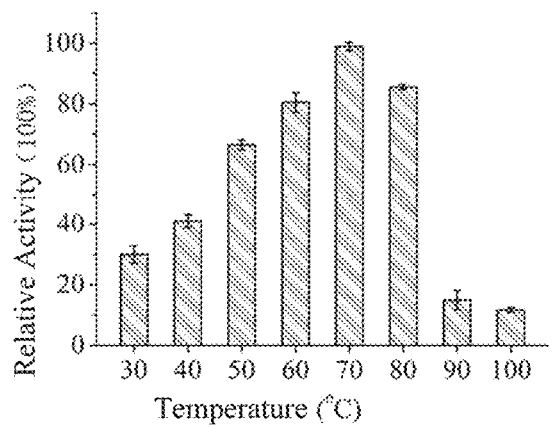
FIG. 4 is a determination result of the optimal reaction temperature of D-lactate dehydrogenase.

2) Determination of the Optimal Reaction Temperature of D-Lactate Dehydrogenases $Ldh_{Ti}$ An enzyme activity determination method is to determine change in NADH at ultraviolet wavelength of 340 nm, and one enzyme activity unit is defined as the enzyme amount needed for oxidizing 1 μmoL of NADH in one minute. Conditions for determination of the optimal reaction temperature of D-lactate dehydrogenases were as follows: 20 mM pyruvic acid as a substrate, 0.2 mM NADH as a coenzyme and 20 mM phosphate buffer solution (pH 7.0) system are adopted; and enzyme activities from 30° C. to 100° C. were respectively determined, and experiments were repeated thrice. A result is as shown in FIG. 4, wherein the optimal reaction temperature of the enzyme is 70° C. Relative enzyme activities in FIG. 4 are relative enzyme activities, which are obtained by: determining enzyme activities at different temperature conditions, and correspondingly converting the enzyme activity values at other temperature conditions on the basis that the highest value at 70° C. is 100%.

Embodiment 3: Preparation of Heat-Resistant *Bacillus licheniformis* Strain

1. Construction of Various Knockout Plasmids in the Present Invention

Figure 5:
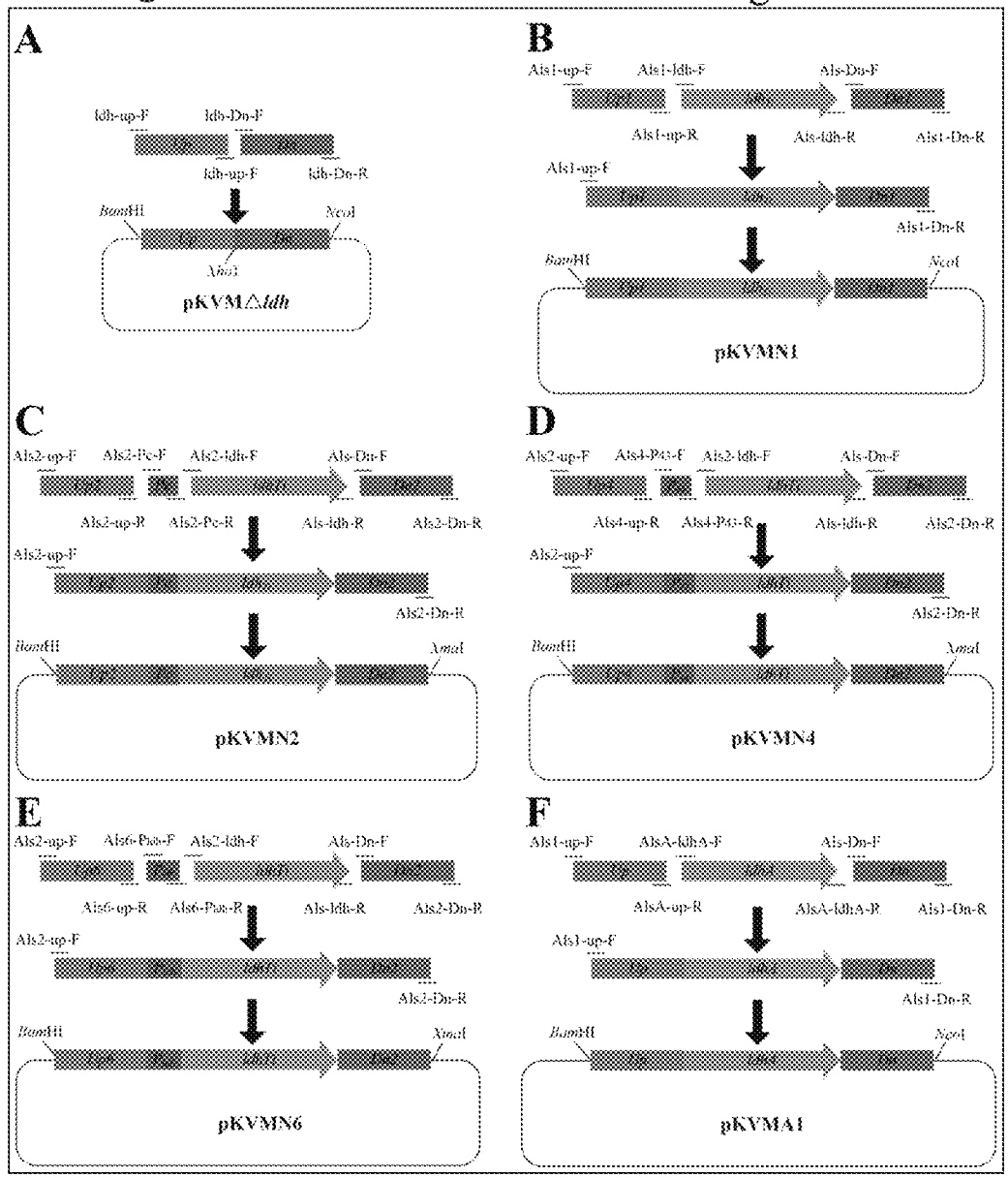
FIG. 5 is construction of various plasmids: A. pKVMΔldh; B. pKVMN1; C. pKVMN2; D. pKVMN4; E. pKVMN6; and F. pKVMA1.

1) Construction of Knockout Plasmids for an L-lactate Dehydrogenase Gene: by using ATCC 14580 genome DNA as a template and primer pairs ldh-up-F/ldh-up-R and ldh-Dn-F/ldh-Dn-R, PCR amplification was performed respectively to upstream and downstream homologous arms of the L-lactate dehydrogenase gene, then the upstream and downstream homologous arms after amplification were respectively subjected to double enzyme digestion with BamHI/XhoI and XhoI/NcoI, simultaneously plasmid pKVM1 was subjected to double enzyme digestion with BamHI/NcoI, the above vector and segments after enzyme digestion were linked by using T$_4$ DNA ligase and transformed into *E. coli* S17-1, and after correctness was verified through DNA sequencing, a positive clone plasmid was named as pKVMΔldh, with plasmid construction as shown in FIG. 5. Herein, the plasmid pKVM1 may be constructed according to the literature Size Unlimited Markerless Deletions by a Transconjugative Plasmid-system in *Bacillus licheniformis* (Rachinger, M. et al., Journal of biotechnology, 2013, 167 (4), 365-369).

2) Construction of Knockout Plasmids for Acetolactate Synthase (alsS) and Acetolactate Decarboxylase (alsD) Genes in Metabolic Pathways of 2,3-butanediol Herein, used primer sequences are as shown in Table 3.

(1) By using ATCC 14580 genome DNA as a template and primer pairs Als1-up-F/Als1-up-R and Als-Dn-F/Als1-Dn-R, PCR amplification was respectively performed to upstream and downstream homologous arms, simultaneously PCR amplification was performed to a D-lactate dehydrogenase Ldh$_{Ti}$ gene by a primer pair Als-ldh-F/Als-ldh-R, and then the above-mentioned three gene segments were fused by primers Als1-up-F and Als1-Dn-R according to a recombinant PCR method. The above-mentioned recombinant PCR product and Als1-Dn-R were respectively subject to double enzyme digestion with enzymes BamHI/NcoI, the product linked by using $T_4$ DNA ligase was transformed into E. coli S17-1, and after correctness was verified through DNA sequencing, a positive clone plasmid was named as pKVMN1 (FIG. 5B). An upstream homologous arm end of this plasmid completely reserved a promoter region ($P_{als}$) of alsS and was directly linked with an original codon "ATG" of ldh$_{Ti}$. Herein, genome sequences of ATCC 14580 may be obtained from NCBI. Herein, a sequence of $P_{als}$ is as expressed by SEQ ID No. 69.

(2) Construction of Knockout Plasmids Using $P_c$ Promoter for Originating ldh$_{Ti}$ Expression: by using plasmid pMMPc as a template and primers Als2-Pc-F and Als2-Pc-R, PCR amplification was performed to obtain a gene of $P_c$ promoter. Herein, the plasmid pMMPc may be constructed from the plasmid pMMB66EH according to the method in the literature New Constitutive Vectors: Useful Genetic Engineering Tools for Biocatalysis (Xu, Y., Tao, F., Ma, C., & Xu, P., Applied And Environmental Microbiology, 2013, 79(8), 2836-2840); and by using ATCC 14580 genome DNA as a template and primer pairs Als2-up-F/Als2-up-R and Als-Dn-F/Als2-Dn-R, PCR amplification was respectively performed to upstream and downstream homologous arms, simultaneously PCR amplification was performed to a D-lactate dehydrogenase Ldh$_{Ti}$ gene by using a primer pair Als2-ldh-F/Als-ldh-R, and then the above-mentioned four gene segments were fused with primers Als2-up-F and Als2-Dn-R according to a recombinant PCR method. The above-mentioned recombinant PCR product and pKVM1 were respectively subjected to double enzyme digestion with enzymes BamHI/XmaI, the product linked by using $T_4$ DNA ligase was transformed into E. coli S17-1, and after correctness was verified through DNA sequencing, a positive clone plasmid was named as pKVMN2 (FIG. 5C). Herein, a sequence of $P_c$ is as expressed by SEQ ID No. 70.

(3) Construction of Knockout Plasmids Using $P_{43}$ Promoter for Originating ldh$_{Ti}$ Expression: by using B. subtilis genome DNA as a template and primers Als4-P43-F and Als4-P43-R, PCR amplification was performed to obtain a gene for the $P_{43}$ promoter, wherein information about $P_{43}$ promoter may be known from the literature Isobutanol Production at Elevated Temperatures in Thermophilic Geobacillus thermoglucosidasius (Lin, P. P., Rabe, K. S., Takasumi, J. L., Kadisch, M., Arnold, F. H., & Liao, J. C., Metabolic Engineering, 2014, 24, 1-8); and by using ATCC 14580 genome DNA as a template and primer pairs Als2-up-F/Als4-up-R and Als-Dn-F/Als2-Dn-R, PCR amplification was respectively performed to upstream and downstream homologous arms, simultaneously PCR amplification was performed to a D-lactate dehydrogenase Ldh$_{Ti}$ gene by using a primer pair Als2-ldh-F/Als-ldh-R, and then the above-mentioned four gene segments were fused by using primers Als2-up-F and Als2-Dn-R according to a recombinant PCR method. The above-mentioned recombinant PCR product and pKVM1 were respectively subjected to double enzyme digestion with enzymes BamHI/XmaI, the product linked by using $T_4$ DNA ligase was transformed into E. coli S17-1, and after correctness was verified through DNA sequencing, a positive clone plasmid was named as pKVMN4 (FIG. 5D). Herein, a sequence of $P_{43}$ is as expressed by SEQ ID No. 71.

(4) Construction of Knockout Plasmids Expressed by Starting ldh$_{Ti}$ with $P_{ldh}$ Promoter: $P_{ldh}$ was a promoter of Bacillus licheniformis ATCC 14580 L-lactate dehydrogenase. By using ATCC 14580 genome DNA as a template and primers Als6-Pldh-F and Als6-Pldh-R, PCR amplification was perform to obtain a gene of the $P_{ldh}$ promoter; and by using primer pairs Als2-up-F/Als6-up-R and Als-Dn-F/Als2-Dn-R, PCR amplification was respectively performed to upstream and downstream homologous arms, simultaneously PCR amplification was performed to a D-lactate dehydrogenase Ldh$_{Ti}$ gene by using a primer pair Als2-ldh-F/Als-ldh-R, and then the above-mentioned four gene segments were fused by using primers Als2-up-F and Als2-Dn-R according to a recombinant PCR method. The above-mentioned recombinant PCR product and pKVM1 was respectively subjected to double enzyme digestion with enzymes BamHI/XmaI, the product linked by using $T_4$ DNA ligase was transformed into E. coli S17-1, and after correctness was verified through DNA sequencing, a positive clone plasmid was named as pKVMN6 (FIG. 5E). Herein, a sequence of $P_{ldh}$ is as expressed by SEQ ID No. 72.

(5) Construction of Knockout Plasmids with Replacing ldh$_{Ti}$ with Mesophilic D-lactate Dehydrogenase Gene: by using ATCC 14580 genome DNA as a template and primer pairs Als1-up-F/AlsA-up-R and Als-Dn-F/Als1-Dn-R, PCR amplification was respectively performed to upstream and downstream homologous arms; and by using E. coli K12 genome DNA as a template and primers AlsA-ldhA-F/AlsA-ldhA-R, PCR amplification was performed to a D-lactate dehydrogenase LdhA gene, and then by using primers Als1-up-F and Als1-Dn-R, the above-mentioned three gene segments were fused according to a recombinant PCR method. The above-mentioned recombinant PCR product and pKVM1 were respectively subjected to double enzyme digestion with enzymes BamHI/NcoI, the product linked by using $T_4$ DNA ligase was transformed into E. coli S17-1, and after correctness was verified through DNA sequencing, a positive clone plasmid was named as pKVMA1 (FIG. 5F).

TABLE 3

Primers used for vector construction

| Name | Sequence (5'-3') |
| --- | --- |
| ldh-up-F | TACGGGATCCTCGGCGACCGATGAACCGAACT (SEQ ID NO: 44) |
| ldh-up-R | TCCGCTCGAGGACTCATCATTCCTTTGCCG (SEQ ID NO: 45) |
| ldh-Dn-F | CCGCTCGAGGGCGTAACTGAACACCATGA (SEQ ID NO: 46) |

TABLE 3-continued

Primers used for vector construction

| Name | Sequence (5'-3') |
|---|---|
| ldh-Dn-R | CATGCCATGGCAAAGAAAGCGATGACCGGCA (SEQ ID NO: 47) |
| Als1-up-F | ACGCGGATCCCTTTGGCAATGACGATCAGCGA (SEQ ID NO: 48) |
| Als1-up-R | TGCATAGAAAAAAAATTACTTTCATAGCCCTCACTCCTCCATTTTCA (SEQ ID NO: 49) |
| Als-Dn-F | ATGAAAAAGCCCTCTTTGAAAAGGGGGC (SEQ ID NO: 50) |
| Als1-Dn-R | CATGCCATGGGGTTTCATAAGACCGCTGATGA (SEQ ID NO: 51) |
| Als1-ldh-F | ATGAAAGTAATTTTTTTTTC (SEQ ID NO: 52) |
| Als-ldh-R | CCCCTTTTCAAAGAGGGCTTTTTCATTTAGATTTCGTTTTTCAGCT (SEQ ID NO: 53) |
| Als2-up-F | ACGCGGATCCGCAAACAGCTGTTCATGAACCG (SEQ ID NO: 54) |
| Als2-up-R | AACGCGCTGTTGTTCTTGTATCGGCACGGGTACATTTGAAGGATCTTG (SEQ ID NO: 55) |
| Als2-Dn-R | TCCCCCCGGGGGTTTCATAAGACCGCTGATGA (SEQ ID NO: 56) |
| Als2-Pc-F | TGCCGATACAAGAACAACAGC (SEQ ID NO: 57) |
| Als2-Pc-R | ATTACTTTCATAGCCCTCACTCCTCCACGGGTTCGCTACCTGCATTA (SEQ ID NO: 58) |
| Als2-ldh-F | GGAGGAGTGAGGGCTATGAAAGTAATTTTTTTTTC (SEQ ID NO: 59) |
| Als4-up-R | TGCCCCGGCCTGCATGCACGTCGACACGGGTACATTTGAAGGATCTTG (SEQ ID NO: 60) |
| Als4-P43-F | TGTCGACGTGCATGCAGGCC (SEQ ID NO: 61) |
| Als4-P43-R | ATTACTTTCATAGCCCTCACTCCTCCTATAATGGTACCGCTATCAC (SEQ ID NO: 62) |
| Als6-up-R | TTTCTTCCTTAAATTTGTACATTTTCCGGGTACATTTGAAGGATCTTG (SEQ ID NO: 63) |
| Als6-Pldh-F | GAAAATGTACAAATTTAAGG (SEQ ID NO: 64) |
| Als6-Pldh-R | ATTACTTTCATAGCCCTCACTCCTCCGACTCATCATTCCTTTGCCG (SEQ ID NO: 65) |
| AlsA-up-R | TTTGTGCTATAAACGGCGAGTTTCATAGCCCTCACTCCTCCATTTTCA (SEQ ID NO: 66) |
| AlsA-ldhA-F | ATGAAACTCGCCGTTTATAGC (SEQ ID NO: 67) |

TABLE 3-continued

Primers used for vector construction

| Name | Sequence (5'-3') |
|---|---|
| AlsA-ldhA-R | CCCCTTTTCAAAGAGGGCTTTTTCATTTAAACCAGTTCGTTCGGGCA (SEQ ID NO: 68) |

Notes:
"-F" represents forward primer; "-R" represents reverse primer; and underlines represent enzyme digestion sites.

3) Construction of Pyruvate Formate-Lyase (PflA) Gene Knockout Plasmids in Pathway of Formic Acid By using ATCC 14580 genome DNA as a template and primer pairs pflA1-F/pflA1-R and pflA2-F/pflA2-R, PCR amplification was respectively performed to upstream and downstream homologous arms of a pyruvate formate-lyase gene, then the upstream and downstream homologous arms were subjected to double enzyme digestion with EcoRI/XhoI and XhoI/BamHIx, simultaneously the plasmid pKVM1 was subjected to double enzyme digestion with BamHI/NcoI, the vector and segments after enzyme digestion were linked by using $T_4$ DNA ligase and then transformed into *E. coli* S17-1, and after correctness was verified through DNA sequencing, a positive clone plasmid was named as pKVMΔpflA.

Herein, primer sequences are as follows (5'-3'):

```
pflA1-F:
                                    (SEQ ID NO: 73)
CCGGAATTCATGGAACAATGGAAAGGT pflA1-R:
                                    (SEQ ID NO: 74)
TCGCTCGAGTGGAAATGTCAAACCCATAG pflA2-F:
                                    (SEQ ID NO: 75)
CCGCTCGAGGACGATGGCCACTGGGATC pflA2-R:
                                    (SEQ ID NO: 76)
ATCGGATCCCTACATCGATTCATGGAAGG
```

4) Construction of Knockout Plasmids for Ethanol Dehydrogenase (AdhB) Gene in Pathway of Ethanol By using ATCC 14580 genome DNA as a template and primer pairs adhB-up-F/adhB-up-R and adhB-dn-F/adhB-dn-R, PCR amplification was respectively performed to upstream and downstream homologous arms of a pyruvate formate-lyase gene, then the upstream and downstream homologous arms were subjected to double enzyme digestion with BamHI/XhoI and XhoI/NcoI, simultaneously the plasmid pKVM1 was subjected to double enzyme digestion with BamHI/NcoI, the vector and segments after enzyme digestion were linked by using $T_4$ DNA ligase and then transformed into *E. coli* S17-1, and after correctness was verified through DNA sequencing, a positive clone plasmid was named as pKVMΔadhB.

Herein, primer sequences are as follows (5'-3'):

```
adhB-up-F:
                                    (SEQ ID NO: 77)
TACGGGATCCGAACGGGAATCGGCAAAGGGATT adhB-up-R:
                                    (SEQ ID NO: 78)
TCCGCTCGAGCGATGATAAAGGCTGCCGAGCTA adhB-dn-F:
                                    (SEQ ID NO: 79)
ACCGCTCGAGTCGTCACACTCCCATTATCG adhB-dn-R:
                                    (SEQ ID NO: 80)
CATGCCATGGCGTCGTATTTGCCGTCAGCT
```

5) Construction of Knockout Plasmids for Acetokinase (Ack) Gene in Pathway of Acetic Acid By using ATCC 14580 genome DNA as a template and primer pairs ack-up-F/ack-up-R and ack-dn-F/ack-dn-R, PCR amplification was respectively performed to upstream and downstream homologous arms of a pyruvate formate-lyase gene, then the upstream and downstream homologous arms were subjected to double enzyme digestion with BamHI/XhoI and XhoI/NcoI, simultaneously the plasmid pKVM1 was subjected to double enzyme digestion with BamHI/NcoI, the vector and segments after enzyme digestion were linked by using $T_4$ DNA ligase and then transformed into *E. coli* S17-1, and after correctness was verified through DNA sequencing, a positive clone plasmid was named as pKVMΔack.

Herein, primer sequences are as follows (5'-3'):

```
ack-up-F:
                                    (SEQ ID NO: 81)
TACGGGATCCGAAGGCTTTCCGGCCTTACT ack-up-R:
                                    (SEQ ID NO: 82)
TCCGCTCGAGCATCGTCATTCCGACGAATG ack-dn-F:
                                    (SEQ ID NO: 83)
ACCGCTCGAGGAGCTTCCAGCATTGATTGC ack-dn-R:
                                    (SEQ ID NO: 84)
CATGCCATGGATGCGGTCATCTGCGATCTT
```

2. Use of the Constructed Vector for Reconstructing Heat-Resistant *Bacillus licheniformis*.

1) Steps for Knocking Out Gene of Heat-Resistant *Bacillus licheniformis*:

(1) *E. coli* S17-1 containing knockout plasmids and *Bacillus licheniformis* MW3 were respectively cultured to $OD_{600\,nm} \approx 1.2$ in LB culture mediums, centrifugal separation was performed for 5 min at 6000 rpm, washing with 0.9% normal saline was performed twice, the two bacterium were mixed, resuspended and centrifugalized, then the bacterium was resuspended by using LB culture mediums, and dropped onto an LB plate, with overnight incubation at 30° C., then the cells were collected by using preheated (30° C.) LB, coated onto an LB solid plate (erythrocin and polymyxin B), and cultured at 30° C.;

(2) Transformants were picked, transferred into LB culture mediums (erythrocin) and cultured at 30° C., the transformants after culture were transferred onto an LB plate (erythrocin and X-Gal) in dilution series and cultured overnight at 42° C., and blue bacterial colonies were correct transformants.

(3) Transformants were picked, transferred into LB culture mediums, and subjected to resistant-free culture at 30° C., cultivated for two generations, diluted and coated onto an LB plate (X-Gal), and white transformants were picked and molecular verification was performed.

2) Preparation Process of Knockout Strain for Heat-Resistant *Bacillus licheniformis*

A host strain selected and used for genetic operation was a mutant strain MW3 in which a restrictive modification system ($\Delta$hsdR1, $\Delta$hsdR2) was knocked out, the mutant strain can perform transformation of exogenous DNA more efficiently, and simultaneously the capabilities of growth and secretion of protein are the same as that of wild ATCC 14580 and are not influenced by knockout. Preparation of a heat-resistant *Bacillus licheniformis* MW3 knockout strain was as follow:

(1) Preparation of host strain BL2 in which L-lactate dehydrogenase (Ldh) gene was knockout: biparental combination was performed to the strain MW3 and *E. coli* S17-1 containing knockout plasmids pKVM$\Delta$ldh by using the above-mentioned genetic operation method, then transformants were obtained respectively through single crossover and double crossover, then a genome was extracted, and verified through PCR, and positive strains were picked and a next experiment was performed.

(2) Preparation of host strain BN11 in which L-lactate dehydrogenase (Ldh) gene, acetolactate synthase (alsS) gene and acetolactate decarboxylase (alsD) gene in pathway of 2,3-butanediol were knockout and promoter $P_{als}$ was reserved: biparental combination was performed to the strain BL2 and *E. coli* S17-1 containing knockout plasmids pKVMN1 by using the above-mentioned genetic operation method, then transformants were obtained respectively through single crossover and double crossover, then a genome was extracted and verified through PCR, and positive strains were picked and a next experiment was performed.

(3) Preparation of host strain BN22 in which L-lactate dehydrogenase (Ldh) gene, acetolactate synthase (alsS) gene and acetolactate decarboxylase (alsD) gene in pathway of 2,3-butanediol were knockout and promoter $P_{als}$ was replaced with promoter $P_c$: biparental combination was performed to the strain BL2 and *E. coli* S17-1 containing knockout plasmids pKVMN2 by using the above-mentioned genetic operation method, then transformants were obtained respectively through single crossover and double crossover, then a genome was extracted and verified through PCR, and positive strains were picked and a next experiment was performed.

(4) Preparation of host strain BN44 in which L-lactate dehydrogenase (Ldh) gene, acetolactate synthase (alsS) gene and acetolactate decarboxylase (alsD) gene in pathway of 2,3-butanediol were knockout and promoter $P_{als}$ was replaced with promoter $P_{43}$: biparental combination was performed to the strain BL2 and *E. coli* S17-1 containing knockout plasmids pKVMN4 by using the above-mentioned genetic operation method, then transformants were obtained respectively through single crossover and double crossover, then a genome was extracted and verified through PCR, and positive strains were picked and a next experiment was performed.

(5) Preparation of host strain BN66 in which L-lactate dehydrogenase (Ldh) gene, acetolactate synthase (alsS) gene and acetolactate decarboxylase (alsD) gene in pathway of 2,3-butanediol were knockout and promoter $P_{als}$ was replaced with promoter $P_{ldh}$: biparental combination was performed to the strain BL2 and *E. coli* S17-1 containing knockout plasmids pKVMN6 by using the above-mentioned genetic operation method, then transformants were obtained respectively through single crossover and double crossover, then a genome was extracted and verified through PCR, and positive strains were picked and a next experiment was performed.

(6) Preparation of host strain BA11 in which thermophilic D-lactate dehydrogenase $Ldh_{Ti}$ in BN11 was replaced with mesophilic D-lactate dehydrogenase: biparental combination was performed to the strain BN11 and *E. coli* S17-1 containing knockout plasmids pKVMA1 by using the above-mentioned genetic operation method, then transformants were obtained respectively through single crossover and double crossover, then a genome was extracted and verified through PCR, and positive strains were picked and a next experiment was performed.

(7) Preparation of host strain BN12 in which pyruvate formate-lyase (PflA) gene was knocked out starting from strain BN11: biparental combination was performed to the strain BN11 and *E. coli* S17-1 containing knockout plasmids pKVM$\Delta$pflA by using the above-mentioned genetic operation method, then transformants were obtained respectively through single crossover and double crossover, then a genome was extracted and verified through PCR, and positive strains were picked and a next experiment was performed.

(8) Preparation of host strain BN13 in which ethanol dehydrogenase (AdhB) gene was knocked out starting from strain BN12: biparental combination was performed to the strain BN11 and *E. coli* S17-1 containing knockout plasmids pKVM$\Delta$adhB by using the above-mentioned genetic operation method, then transformants were obtained respectively through single crossover and double crossover, then a genome was extracted and verified through PCR, and positive strains were picked and a next experiment was performed.

(9) Preparation of host strain BN13 in which acetokinase (Ack) gene was knocked out starting from strain BN13: biparental combination was performed to the strain BN11 and *E. coli* S17-1 containing knockout plasmids pKVM$\Delta$ack by using the above-mentioned genetic operation method, then transformants were obtained respectively through single crossover and double crossover, then a genome was extracted and verified through PCR, and positive strains were selected and a next experiment was performed.

Embodiment 4: Fermentation of Original Strain, Ldh-Knocked-Out Strain and Strains Containing Different Promoters and Gene $ldh_{Ti}$ This embodiment was performed in a 5 L full-automatic fermentation tank, and components of various used culture mediums were as follows:

Each liter of slant culture mediums contained: 30-50 g of glucose, 5-10 g of yeast powder, 2-8 g of peptone, 30 g of calcium carbonate, 15-25 g of agar powder and balance of water. pH of the slant culture mediums was 7.0. Sterilization was performed for 15 min at 115° C.

Each liter of seed culture mediums contained: 40-120 g of glucose, 5-10 g of yeast powder, 2-8 g of peptone, 50 g of calcium carbonate and balance of water. pH of the seed culture mediums was 6.0-8.0. Sterilization was performed for 15 min at 115° C.

Each liter of fermentation culture mediums contained: 120 g of glucose, 5-10 g of yeast powder, 2-8 g of peptone, 50 g of calcium carbonate and balance of water. pH of the fermentation culture mediums was 6.5-7.5. Sterilization was performed for 15 min at 115° C.

The method for producing D-lactic acid through fermentation in this embodiment comprised the following steps:

(1) Slant culture: the strain was inoculated into the slant culture mediums and cultured for 24 h at 50° C.

(2) Seed culture: the strains cultured in step (1) were inoculated into a 40 mL triangular flask containing 40 mL of seed culture mediums under aseptic conditions by using an inoculating loop for two times, and subjected to static culture for 24 h at 50° C. to obtain seed culture solution 1; and 10 mL seed culture solution 1 was inoculated into a 500 mL triangular flask containing 100 mL seed culture medium under aseptic conditions, and subjected to static culture for 24 h at 50° C. to obtain seed culture solution 2.

(3) Fermentation culture: 300 mL seed culture solution 2 prepared in step (2) was inoculated into a fermentation tank containing 2.7 L fermentation culture mediums under aseptic conditions, and subjected to culture at 50° C. under stirring at 70 rpm, sampling was performed once every 3 h, and fermentation was ended after 12 h.

Figure 6:
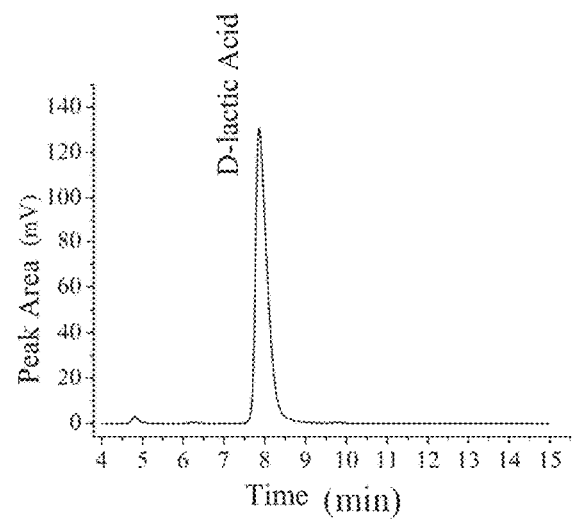
FIG. 6 is optical purity analysis by HPLC for D-lactic acid produced by strains BN11.

After fermentation was ended, supernatant of the fermentation liquid was taken and analyzed for concentrations of D-lactic acid, byproducts and total reducing sugar through HPLC, and sugar-acid conversion rate was calculated (Table 4), wherein conversion rate (%)=yield of lactic acid (g/L)/consumption of glucose (g/L)*100%. Herein, through HPLC for detecting D-lactic acid and L-lactic acid, it can be seen that the optical purity of D-lactic acid produced by BN11 can reach 99.9% (FIG. 6).

pathway is high, and Pals is a promoter of a first acetolactate synthase gene in a gene cluster for synthesis of 2,3-butanediol, this is possibly the reason why the gene engineering strain BN11 (adopting the promoter) presents a good conversion rate.

Embodiment 5: Fermentation of an Optimal Strain in Embodiment 4 after Blocking of Byproduct Production This embodiment was performed in a 5 L full-automatic fermentation tank, the used strains included BN11, BN12 (with a pathway for producing byproduct formic acid blocked), BN13 (with pathways for producing byproducts formic acid and ethanol blocked) and BN14 (with pathways for producing byproducts formic acid, ethanol and acetic acid blocked), and components of various used culture mediums were as follows:

Slant culture mediums, seed culture mediums and fermentation culture mediums were the same as that in Embodiment 4.

A method for producing D-lactic acid through fermentation was the same as that in Embodiment 4.

After fermentation was ended, supernatant of the fermentation liquid was taken and analyzed for concentrations of D-lactic acid, byproducts and total reducing sugar through HPLC, and sugar-acid conversion rate was calculated (Table 5), wherein conversion rate (%)=yield of lactic acid (g/L)/consumption of glucose (g/L)*100%. Herein, through

TABLE 4

Glucose Consumption and Product Production for Different Strains

| Strain | Glucose Consumption (g/L) | Product (g/L) | | | | | | Conversion Rate (%) |
|---|---|---|---|---|---|---|---|---|
| | | 2,3-butanediol | L-lactic Acid | D-lactic Acid | Formic Acid | Acetic Acid | Ethanol | |
| MW3 | 42.9 | 11.4 | 7.6 | — | 3.7 | 1.9 | 3.0 | 17.7 |
| BL2 | 52.1 | 18.4 | — | — | 4.8 | 2.7 | 3.3 | — |
| BN11 | 85.1 | — | — | 76.8 | 2.1 | 2.7 | 1.8 | 90.2 |
| BN22 | 17.5 | — | — | 0.52 | 4.1 | 3.2 | 2.9 | 3.0 |
| BN44 | 55.0 | — | — | 35.9 | 4.5 | 3.8 | 5.0 | 65.3 |
| BN66 | 45.3 | — | — | 8.1 | 12.3 | 4.7 | 5.4 | 17.9 |

"—" represents that the amount of product is smaller than 0.01 g/L.

Since the original strain *Bacillus licheniformis* ATCC 14580 adopted in this embodiment can produces 2,3-butanediol with a high yield, i.e., it indicates that the activity of this HPLC for detecting D-lactic acid and L-lactic acid, it can be seen that the optical purity of D-lactic acid produced by BN11 can reach 99.9%.

TABLE 5

Glucose Consumption and Product Production of Different Strains with Pathways for Producing Byproducts Blocked

| Strain | Glucose Consumption (g/L) | Product (g/L) | | | | | | Conversion Rate (%) |
|---|---|---|---|---|---|---|---|---|
| | | 2,3-butanediol | L-lactic Acid | D-lactic Acid | Formic Acid | Acetic Acid | Ethanol | |
| BN11 | 85.1 | — | — | 76.8 | 2.1 | 2.7 | 1.8 | 90.2 |
| BN12 | 85.2 | — | — | 77.5 | 1.0 | 2.8 | 1.7 | 91.0 |
| BN13 | 85.1 | — | — | 79.0 | 1.1 | 2.7 | 0.1 | 92.8 |
| BN14 | 85.3 | — | — | 80.5 | 1.0 | 1.2 | 0.1 | 94.4 |

"—" represents that the amount of product is smaller than 0.01 g/L.

As shown by results, after generation of 2,3-butanediol and L-lactic acid is blocked, by further blocking pathways for producing other byproducts, the conversion rate from glucose to D-lactic acid can be improved. In addition, the more the blocked pathways are, the higher the conversion rate of D-lactic acid is.

Embodiment 6: Optimization of Fermentation Conditions of Optimal Strain in Embodiment 4

This embodiment was performed in a 5 L full-automatic fermentation tank, the used strain was BN11, and components of various used culture mediums were as follows:

Slant culture mediums and the seed culture mediums were the same as that in Embodiment 4.

Each liter of fermentation culture mediums contained: 1) 90 g of glucose, 5-10 g of yeast powder, 2-8 g of peptone and balance of water when the optimal fermentation pH was determined, wherein pH was respectively regulated to 6.0, 6.5, 7.0, 7.5 and 8.0; and 2) 5-10 g of yeast powder, 2-8 g of peptone, 60 g, 87 g, 122 g, 148 g, 180 g and 202 g of glucose and balance of water in order to determine capabilities of the strain in producing D-lactic acid in culture mediums with different concentrations of glucose.

The method for producing D-lactic acid through fermentation in this embodiment comprised the following steps:

(1) Slant culture: same as that in Embodiment 4.

(2) Seed culture: same as that in Embodiment 4.

(3) Fermentation culture: 300 mL of seed culture solution 2 prepared in step (2) was inoculated into a fermentation tank containing 2.7 L of different fermentation culture mediums under aseptic conditions, and cultured at 50° C. under stirring at 70 rpm, sampling was performed once every 3 h, and fermentation was ended after 12 h.

After fermentation was ended, supernatant of the fermentation liquid was taken and analyzed for concentrations of D-lactic acid, byproducts and total reducing sugar through HPLC, and sugar-acid conversion rate was calculated.

Figure 7:
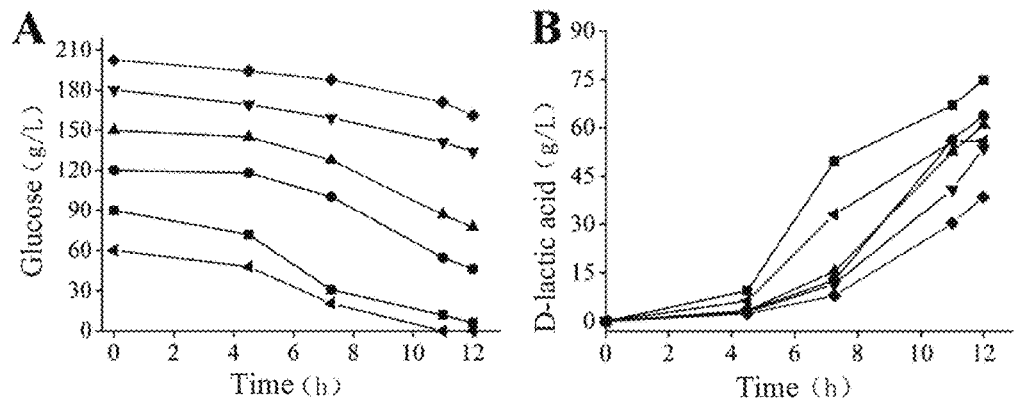
FIG. 7 shows situations that strains BN11 use glucose with different concentrations to produce D-lactic acid through fermentation: A. situations for consumption of sugar with different concentrations; and B. situations for D-lactic acid produced by using sugar with different concentrations. Initial sugar concentration: ◂, 60.0 g/L; ■, 87.0 g/L; ●, 122.0 g/L; ▲, 148.0 g/L; ▼, 180.0 g/L; and ♦, 202.0 g/L.

As proved by experiment results, the optimal fermentation pH for the experiment strain BN11 at 50° C. is 7.0; and at the pH value, the consumption speed of glucose was the largest, the sugar-acid conversion rate is the highest and the amount of the byproducts is the least (Table 6). From FIG. 7, it can be seen that, when the concentration of glucose does not exceed 180 g/L, the speed at which the strain BN11 consumes glucose or produces D-lactic is not obviously inhibited; and when the concentration of glucose is higher than 180 g/L such 202 g/L, the consumption of glucose is obviously inhibited and the production speed of D-lactic acid is reduced accordingly.

Embodiment 7: Production of D-Lactic Acid by Using Optimal Strain in Embodiment 4 Through Batch Fermentation and Fed (Sugar)-Batch Fermentation This embodiment was performed in a 5 L full-automatic fermentation tank, the used strain was BN11, and components of various used culture mediums were as follows:

The slant culture mediums and the seed culture mediums were the same as that in Embodiment 4.

Each liter of fermentation culture mediums contained: 1) 180 g of glucose, 5-10 g of yeast powder, 2-8 g of peptone and balance of water when D-lactic acid was produced through batch fermentation; and 2) 40-70 g of glucose, 5-10 g of yeast powder, 2-8 g of peptone and balance of water when D-lactic acid was produced through fed (sugar)-batch fermentation.

The method for producing D-lactic acid through fermentation in this embodiment comprised the following steps:

(1) Slant culture: same as that in Embodiment 4.

(2) Seed culture: same as that in Embodiment 4.

(3) Fermentation culture: 300 mL of seed culture solution 2 prepared in step (2) was inoculated into fermentation tanks respectively containing 2.7 L of batch fermentation culture mediums and fed (sugar)-batch fermentation culture mediums under aseptic conditions, and cultured at 50° C. under stirring at 70 rpm, sampling was performed once every 2-5 h, and the amount of residual sugar in the fermentation liquid was determined. During batch fermentation, when glucose was fully consumed or the consumption speed tended to 0 in the fermentation process, fermentation was ended; and during fed (sugar)-batch fermentation, when the concentration of glucose decreased to 10-20 g/L, glucose was fed in batch to enable the concentration of glucose to reach 50-70 g/L, and totally the glucose was supplemented for 2-5 times. When the consumption speed of glucose in the fermentation process tended to 0, fermentation was ended.

After fermentation is ended, supernatant of the fermentation liquid was taken and analyzed for concentrations of D-lactic acid, byproducts and total reducing sugar through HPLC, and sugar-acid conversion rate and production speed were calculated.

Figure 8:
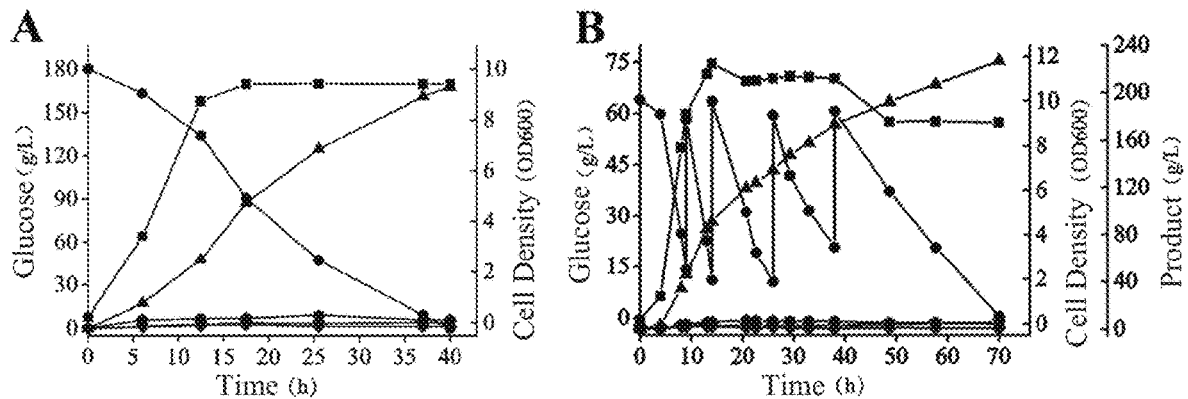
FIG. 8 is shows situations that strains BN11 produce D-lactic acid through batch fermentation and fed (glucose)-batch fermentation: A. batch fermentation results; and B. fed (glucose)-batch fermentation results. ■, cell density; ●, glucose; ▲, D-lactic acid; ♦, formic acid; ▼, acetic acid; and ★, ethanol.

From FIG. 8A, it can be seen that, when batch fermentation is performed by using the experiment strain BN11 at 50° C., glucose is fully consumed and fermentation is ended after 40 h. The concentration of the produced D-lactic acid is 167.7 g/L, the concentration of the byproduct ethanol is 5.8 g/L, the concentration of formic acid is 1.1 g/L and the

TABLE 6

Influence of pH on Production of D-lactic Acid by BN11

| pH | Cell Density ($OD_{600\ nm}$) | Glucose Consumption (g/L) | Product (g/L) | | | | Conversion Rate (%) |
|---|---|---|---|---|---|---|---|
| | | | D-lactic Acid | Formic Acid | Acetic Acid | Ethanol | |
| 6.0 | 3.3 | 19.8 | 16.9 | — | 0.90 | 0.51 | 85.3 |
| 6.5 | 9.1 | 55.4 | 49.1 | 0.30 | 2.6 | 0.72 | 88.6 |
| 7.0 | 10.5 | 86.1 | 77.8 | 2.6 | 3.6 | 1.8 | 90.4 |
| 7.5 | 10.2 | 83.4 | 67.6 | 6.5 | 5.4 | 1.0 | 81.1 |
| 8.0 | 9.3 | 71.7 | 55.2 | 5.9 | 4.6 | 1.6 | 77.0 |

"—" represents that the amount of product is smaller than 0.01 g/L.

concentration of acetic acid is 3.6 g/L. The sugar-acid conversion rate and the production speed are respectively 93.0% and 4.2 g/[L·h].

From FIG. 8B, it can be seen that, when fed (sugar)-batch fermentation is performed by using the strain BN11 at 50° C., totally glucose is fed for four times and fermentation is ended after 70 h, wherein in the first 38 h, 173.2 g/L D-lactic acid is produced and the production speed is 4.6 g/[L·h]; and from 38 h to 70 h, the concentration of D-lactic acid increases from 173.2 g/L to 226.6 g/L, and the production speed is 1.7 g/[L·h]. After fermentation is ended, totally 242.1 g/L glucose is consumed, the average production speed is 3.2 g/[L·h] and the sugar-acid conversion rate is 93.6%. The final concentration of the byproduct formic acid is 0.56 g/L, and the final concentrations of acetic acid and ethanol are respectively 5.5 g/L and 4.3 g/L.

Embodiment 8: Production of D-Lactic Acid by Using Strain in which Thermophilic $Ldh_n$ is Replaced with Mesophilic D-Lactate Dehydrogenase (Ldha) Through Batch Fermentation and Fed (Sugar)-Batch Fermentation This embodiment was performed in a 5 L full-automatic fermentation tank, the used strain was BA11, and components of various used culture mediums were as follows:

Slant culture mediums and seed culture mediums were the same as that in Embodiment 4.

The content contained in each liter of fermentation culture mediums was the same as that in Embodiment 7.

The method for producing D-lactic acid through fermentation in this embodiment comprised the following steps:
(1) Slant culture: same as that in Embodiment 4.
(2) Seed culture: same as that in Embodiment 4.
(3) Fermentation culture: same as that in Embodiment 7.

After fermentation was ended, supernatant of the fermentation liquid was taken and analyzed for concentrations of D-lactic acid, byproducts and total reducing sugar through HPLC, and sugar-acid conversion rate and production speed were calculated.

Figure 9:
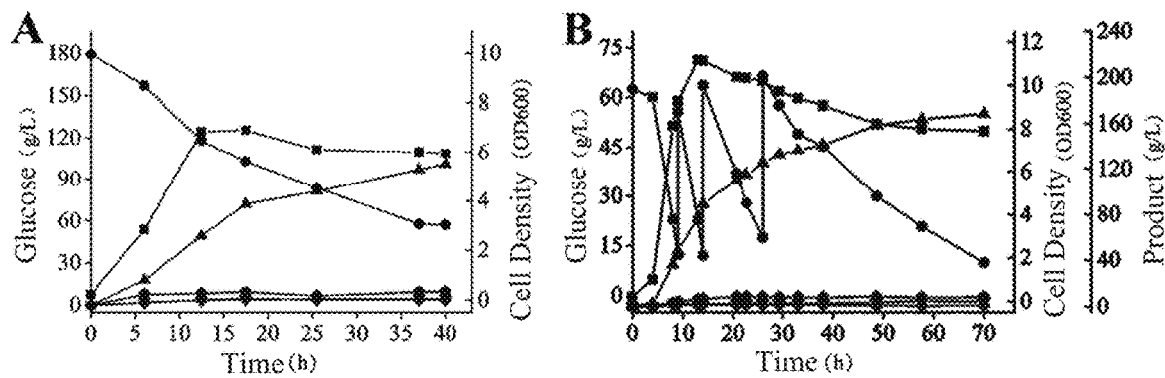
FIG. 9 is shows situations that strains BAH produce D-lactic acid through batch fermentation and fed (glucose)-batch fermentation: A. batch fermentation results; and B. fed (glucose)-batch fermentation results. ■, cell density; ●, glucose; ▲, D-lactic acid; ♦, formic acid; ▼, acetic acid; and ★, ethanol.

From FIG. 9A, it can be seen that, when batch fermentation is performed by using the experiment strain BA11 at 50° C., fermentation is ended after 40 h and the concentration of remaining residual sugar is 57.1 g/L. The concentration of the finally produced D-lactic acid is 100.8 g/L, the concentration of the byproduct ethanol is 9.5 g/L, the concentration of formic acid is 3.9 g/L and the concentration of acetic acid is 4.5 g/L. The sugar-acid conversion rate and the production speed are respectively 82.4% and 2.5 g/[L·h].

From FIG. 9B, it can be seen that, when fed (sugar)-batch fermentation is performed by using the strain BA11 at 50° C., totally glucose is fed for three times and fermentation is ended after 70 h. Finally, totally 196.9 g/L glucose is consumed, the produced D-lactic acid is 168.6 g/L, the average production speed is 2.4 g/[L·h] and the sugar-acid conversion rate is 85.6%. The final concentrations of the byproducts formic acid and ethanol are 1.0 g/L, and the final concentration of acetic acid is 5.5 g/L.

Embodiment 9: Production of D-Lactic Acid by Using Optimal Strain in Embodiment 4 Through Fed-Batch Fermentation by Using Xylose This embodiment was performed in a 5 L full-automatic fermentation tank, the used strain was BN11, and components of various used culture mediums were as follows:

Each liter of slant culture mediums contained: 30-50 g of xylose, 5-10 g of yeast powder, 2-8 g of peptone, 30 g of calcium carbonate, 15-25 g of agar powder and balance of water. pH of the slant culture mediums was 7.0. Sterilization was performed for 15 min at 115° C.

Each liter of seed culture mediums contained: 40-70 g of xylose, 5-10 g of yeast powder, 2-8 g of peptone, 50 g of calcium carbonate and balance of water. pH of the seed culture mediums was 6.0-8.0. Sterilization was performed for 15 min at 115° C.

Each liter of fermentation culture mediums contained: 40-60 g of xylose, 5-10 g of yeast powder, 2-8 g of peptone and balance of water. pH of the fermentation culture mediums was 6.5-7.5. Sterilization was performed for 15 min at 115° C.

The method for producing D-lactic acid through fermentation in this embodiment comprised the following steps:
(1) Slant culture: same as that in Embodiment 4.
(2) Seed culture: same as that in Embodiment 4.
(3) Fermentation culture: 300 mL of seed culture solution prepared in step (2) was inoculated into a fermentation tank containing 2.7 L of fermentation culture mediums under aseptic conditions, and cultured at 50° C. under stirring at 70 rpm, sampling was performed once every 2-5 h, and the amount of residual sugar in the fermentation liquid was determined. When the concentration of xylose decreased to 10-20 g/L, xylose was fed in batch to enable the concentration of xylose to reach 40-60 g/L, and totally the xylose was supplemented for 2-5 times. When the consumption speed of xylose in the fermentation process tended to 0, fermentation was ended.

After fermentation was ended, supernatant of the fermentation liquid was taken and analyzed for concentrations of D-lactic acid, byproducts and total reducing sugar through HPLC, and sugar-acid conversion rate and production speed were calculated.

Figures 10, 11:
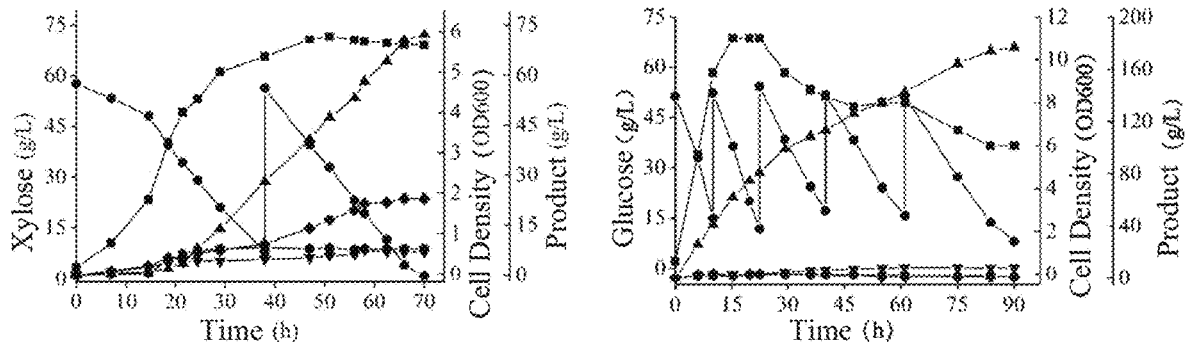
FIG. 10 is shows situations that strains BN11 produce D-lactic acid through fed-batch fermentation by using xylose. ■, cell density; ●, xylose; ▲, D-lactic acid; ♦, formic acid; ▼, acetic acid; and ★, ethanol.
FIG. 11 shows situations that strains BN11 produce D-lactic acid through fed (glucose)-batch fermentation by using low-cost culture mediums. ■, cell density; ●, glucose; ▲, D-lactic acid; ♦, formic acid; ▼, acetic acid; and ★, ethanol.

From FIG. 10, it can be see that, when fed-batch fermentation is performed by using the strain BN11 and xylose as a carbon source at 50° C., totally xylose is supplemented once and fermentation is ended after 70 h. Finally, totally 114.7 g/L xylose is consumed, the produced D-lactic acid is 72.1 g/L, and the average production speed is 1.0 g/[L·h]. The final concentration of the byproduct formic acid is 23.0 g/L, and the final concentrations of acetic acid and ethanol are respectively 7.2 g/L and 8 g/L.

Embodiment 10: Production of D-Lactic Acid by Using Optimal Strain in Embodiment 4 Through Fed (Sugar)-Batch Fermentation by Using Low-Cost Culture Mediums This embodiment was performed in a 5 L full-automatic fermentation tank, the used strain was BN11, and components of various used culture mediums were as follows:

Slant culture mediums and seed culture mediums were the same as that in Embodiment 4.

Each liter of fermentation culture mediums contained: 1) 40-70 g of glucose, 1-5 g of yeast powder, 0.25-1.0 g/L potassium dihydrogen phosphate, 0.25-1.0 g/L dipotassium phosphate, 1.5-10.0 g/L ammonium sulfate, 1.2-5.0 g/L diammonium hydrogen phosphate, 0.15-0.8 g/L zinc sulfate, 1-10 g/L dried corn steep powder and balance of water. Sterilization was performed for 15 min at 115° C.

The method for producing D-lactic acid through fermentation in this embodiment comprised the following steps:
(1) Slant culture: same as that in Embodiment 4.
(2) Seed culture: same as that in Embodiment 4.

(3) Fermentation culture: 600 mL of seed culture solution 2 prepared in step (2) was inoculated into a fermentation tank containing 2.4 L of low-cost fermentation culture mediums under aseptic conditions, and cultured at 50° C. under stirring at 70 rpm, sampling was performed once every 2-5 h, and the amount of residual sugar in the fermentation liquid was determined. When the concentration of glucose decreased to 10-20 g/L, glucose was fed in batch to enable the concentration of glucose to reach 50-70 g/L, and totally the glucose was supplemented for 2-5 times. When the consumption speed of glucose in the fermentation process tended to 0, fermentation was ended.

After fermentation was ended, supernatant of the fermentation liquid was taken and analyzed for concentrations of D-lactic acid, byproducts and total reducing sugar through HPLC, and sugar-acid conversion rate and production speed were calculated.

From FIG. 11, it can be seen that, when fed (sugar)-batch fermentation is performed by using the strain BN11 and low-cost culture mediums at 50° C., totally glucose is fed in batch for four times and fermentation is ended after 90 h. Totally 190.9 g/L glucose is consumed, the produced D-lactic acid is 175.7 g/L, the average production speed is 2.0 g/[L·h] and the sugar-acid conversion rate is 92.0%. The final concentration of the byproduct acetic acid is 7.5 g/L, and the final concentrations of formic acid and ethanol are respectively 0.62 g/L and 1.6 g/L.

The preferred embodiments of the present invention are described above. It shall be understood that one skilled in the art may make various modifications and variations according to the concept of the present invention without contributing any inventive labor. Therefore, all technical solutions obtained by one skilled in the art according to the concept of the present invention on the basis of the prior art in combination with logical analysis, reasoning or limited experiments shall be included in the protective scope determined by the claims.

The invention claimed is:

1. A D-lactate dehydrogenase comprising a substitution, deletion, insertion, addition of one or more amino acid residues, wherein said D-lactate dehydrogenase comprises an amino acid sequence having at least 80% and less than 100% sequence identity to SEQ ID NO: 1, and wherein said D-lactate dehydrogenase has D-lactate dehydrogenase activity.

2. The D-lactate dehydrogenase according to claim 1, wherein the substitution, deletion, insertion or addition of the amino acid residues occurs outside a functional domain comprising enzyme catalytic sites, ligand binding sites and NAD binding sites of the D-lactate dehydrogenase.

3. The D-lactate dehydrogenase according to claim 2, wherein, according to relative positions, key amino acids at the enzyme catalytic sites are Arg at position 229, Glu at position 258 and His at position 290; key amino acids at the ligand binding sites are Ser, Ala and Gly at positions 75-77, Tyr at position 99, Arg at position 229, His at position 290 and Phe at position 293; and key amino acids at the NAD binding sites are Tyr position 99, Ile at position 104, Gly at position 150, Gly, Lys, Ile and Gly at positions 152-155, Tyr, Asp and Pro at positions 172-174, His, Cys, Pro and Leu at positions 199-202, Asn at position 206, Met at position 209, Thr, Ala and Arg at positions 227-229, Asp and Val at positions 253 and 254, His at position 290, and Ala and Phe at positions 292 and 293.

4. The D-lactate dehydrogenase according to claim 1, wherein said substitution is a conservative substitution.

* * * * *